United States Patent
Palmer et al.

(10) Patent No.: US 8,202,535 B2
(45) Date of Patent: Jun. 19, 2012

(54) SMALL-VOLUME ORAL TRANSMUCOSAL DOSAGE FORMS

(75) Inventors: Pamela Palmer, San Francisco, CA (US); Thomas Schreck, Portola Valley, CA (US); Stelios Tzannis, Newark, CA (US); Larry Hamel, Mountain View, CA (US); Andrew I. Poutiatine, San Anselmo, CA (US)

(73) Assignee: Acelrx Pharmaceuticals, Inc., Redwood City, CA (US)

( * ) Notice: Subject to any disclaimer, the term of this patent is extended or adjusted under 35 U.S.C. 154(b) by 1386 days.

(21) Appl. No.: 11/650,174

(22) Filed: Jan. 5, 2007

(65) Prior Publication Data

US 2010/0256190 A1  Oct. 7, 2010

Related U.S. Application Data

(60) Provisional application No. 60/756,937, filed on Jan. 6, 2006.

(51) Int. Cl.
*A61K 9/20* (2006.01)
(52) U.S. Cl. .................................................. 424/464
(58) Field of Classification Search .................. None
See application file for complete search history.

(56) References Cited

U.S. PATENT DOCUMENTS

| | | | |
|---|---|---|---|
| 2,621,655 A | 12/1952 | Olson | |
| 4,671,953 A | 6/1987 | Stanley | |
| 4,863,737 A | 9/1989 | Stanley | |
| 5,080,903 A | 1/1992 | Ayache | |
| 5,132,114 A | 7/1992 | Stanley | |
| 5,178,878 A | 1/1993 | Wehling | |
| 5,236,714 A | 8/1993 | Lee | |
| 5,288,497 A | 2/1994 | Stanley | |
| 5,288,498 A | 2/1994 | Stanley | |
| 5,296,234 A | 3/1994 | Hadaway | |
| 5,657,748 A | 8/1997 | Braithwaite | |
| 5,785,989 A | 7/1998 | Stanley | |
| 5,968,547 A | 10/1999 | Reder | |
| 5,997,518 A | 12/1999 | Laibovitz | |
| 6,200,604 B1 | 3/2001 | Pather | |
| 6,216,033 B1 | 4/2001 | Southam et al. | |
| 6,264,981 B1 | 7/2001 | Zhang et al. | |
| 6,310,072 B1 | 10/2001 | Smith | |
| 6,319,510 B1 | 11/2001 | Yates | |
| 6,350,470 B1 | 2/2002 | Pather | |
| 6,391,335 B1 | 5/2002 | Pather | |
| 6,500,456 B1 | 12/2002 | Capella | |

(Continued)

FOREIGN PATENT DOCUMENTS

WO    WO 00/16750    3/2000

(Continued)

OTHER PUBLICATIONS

Siepmann et al. "Calculation of the requried size and shape of hydroxypropyl methylcellulose matrices to achieve desired drug release profiles", Int. J. Pharma., 2000, 201(1), p. 151-164.*

(Continued)

*Primary Examiner* — Bethany Barham
(74) *Attorney, Agent, or Firm* — Cooley LLP

(57) ABSTRACT

Small-volume oral transmucosal dosage forms or Nano-Tabs® comprising a predetermined amount of a pharmaceutically active drug are provided. Exemplary applications include use of the NanoTabs® to administer a drug for the treatment of acute, post-operative or breakthrough pain.

27 Claims, 7 Drawing Sheets

U.S. PATENT DOCUMENTS

| | | | |
|---|---|---|---|
| 6,509,036 | B2 | 1/2003 | Pather |
| 6,641,838 | B2 | 11/2003 | Pather |
| 6,680,071 | B1 | 1/2004 | Johnson et al. |
| 6,759,059 | B1 | 7/2004 | Pettersson |
| 6,761,910 | B1 | 7/2004 | Pettersson |
| 6,764,696 | B2 | 7/2004 | Pather |
| 6,974,590 | B2 | 12/2005 | Pather |
| 7,074,935 | B2 | 7/2006 | Mathew |
| 7,090,866 | B2 | 8/2006 | Johnson |
| 7,208,604 | B2 | 4/2007 | Mathew |
| 7,484,642 | B2 | 2/2009 | Bonney et al. |
| 7,500,444 | B2 | 3/2009 | Bonney et al. |
| 7,552,728 | B2 | 6/2009 | Bonney et al. |
| 2002/0071857 | A1 | 6/2002 | Kararli et al. |
| 2002/0160043 | A1 | 10/2002 | Coleman |
| 2003/0035776 | A1 | 2/2003 | Hodges |
| 2003/0091629 | A1 | 5/2003 | Pather et al. |
| 2003/0099158 | A1 | 5/2003 | De La Huerga |
| 2003/0130314 | A1 | 7/2003 | Druzgala |
| 2003/0132239 | A1 | 7/2003 | Konig |
| 2004/0025871 | A1 | 2/2004 | Davies |
| 2004/0034059 | A1* | 2/2004 | Grarup et al. ............ 514/317 |
| 2004/0037882 | A1 | 2/2004 | Johnson |
| 2004/0120896 | A1 | 6/2004 | Dugger |
| 2004/0180080 | A1 | 9/2004 | Furusawa |
| 2004/0213855 | A1 | 10/2004 | Pettersson |
| 2004/0253307 | A1 | 12/2004 | Hague et al. |
| 2005/0038062 | A1 | 2/2005 | Burns |
| 2005/0064030 | A1 | 3/2005 | Pather et al. |
| 2005/0129737 | A1 | 6/2005 | Johnson |
| 2005/0142197 | A1 | 6/2005 | Moe |
| 2005/0142198 | A1 | 6/2005 | Moe |
| 2005/0163838 | A1 | 7/2005 | Moe |
| 2005/0176790 | A1* | 8/2005 | Bartholomaus et al. ...... 514/373 |
| 2006/0045865 | A1 | 3/2006 | Jacob |
| 2006/0067978 | A1 | 3/2006 | Heiler |
| 2006/0216352 | A1* | 9/2006 | Nystrom et al. ............ 424/489 |
| 2006/0292219 | A1 | 12/2006 | Pather |
| 2007/0020186 | A1 | 1/2007 | Stroppolo |
| 2007/0031502 | A1 | 2/2007 | Pettersson |
| 2007/0036853 | A1 | 2/2007 | Agarwal |

FOREIGN PATENT DOCUMENTS

| | | |
|---|---|---|
| WO | WO 00/57858 | 10/2000 |
| WO | WO 01/30288 | 5/2001 |
| WO | WO 02/067916 A2 | 9/2002 |
| WO | WO 2004/069198 | 8/2004 |

OTHER PUBLICATIONS

Restriction Requirement for U.S. Appl. No. 11/825,212, mailed Dec. 9, 2009.
Office Action for U.S. Appl. No. 11/825,251, mailed Dec. 15, 2009.
Office Action for U.S. Appl. No. 11/650,227, mailed Dec. 15, 2009.
Office Action for U.S. Appl. No. 11/429,904, mailed Aug. 20, 2009.
Office Action for U.S. Appl. No. 11/473,551, mailed Sep. 11, 2009.
Office Action for U.S. Appl. No. 11/650,227, mailed Sep. 21, 2009.
Office Action for U.S. Appl. No. 11/650,230, mailed Aug. 4, 2009.
Office Action for U.S. Appl. No. 11/974,092, mailed Sep. 30, 2009.
International Search Report and Written Opinion dated Dec. 17, 2007 issued in PCT/2007/00527 (WO/2007/081947).
International Search Report and Written Opinion dated Feb. 4, 2008 issued in PCT/2007/00528 (WO/2007/081948).
Bredenberg et al; "In vitro and in vivo evaluation of a new sublingual tablet system for rapid or mucosal absorption using fentanyl citrate as the active substance"; *European Journal of Pharmaceutical Sciences*; 2003; 327-334.
Darwish et al.; "Bioequivalence following buccal and sublingual placement of fentanyl buccal tablet 400mcg in healthy subjects"; *Clin. Drug Invest.* 2008: 28(1): 1-7.
Darwish et al.; "Effect of buccal dwell time on the pharmacokinetic profile of fentanyl buccal tablet"; *Expert Opin Pharmacother* Sep. 2007;8(13):2011-6. Review.
Darwish et al.; "Comparison of equivalent doses of fentanyl buccal tablets and arteriovenous differences in fentanyl pharmacokinetics"; *Clinical Pharmacokinetics*; 2006; 45(8): 843-50.
Darwish et al.; "Relative bioavailability of the fentanyl effervescent buccal tablet (FEBT) 1,080 pg versus oral transmucosal fentanyl citrate 1,600 pg and dose proportionality of FEBT 270 to 1,300 microg: a single dose, randomized, open-label, three period study in healthy adult volunteers"; *Clinical Therapies*; 2006; 28(5):715-24.
Darwish et al.; "Pharmacokinetics and dose proportionality of fentanyl effervescent buccal tablets in healthy volunteers"; *Clinical Pharmacokinetics*; 2005; 44(12): 1279-86.
KGH Drug Information Service; "Sublingual Sufentanil for Incident Pain"; *KGH Drug Information Bulletin*, vol. 37(4) 2, 2004.
Yeomans et al.; "Sublingual Sufentanil"; *Vancouver Hospital and Health Science Center Drug and Therapeutics Newsletter*, vol. 8(1) 2, 2001.
Gulledge, Office Action for U.S. Appl. No. 11/825,251, 12 pages, United States Patent and Trademark Office (mailed Aug. 5, 2010).
Gulledge, Office Action for U.S. Appl. No. 11/825,251, 9 pages, United States Patent and Trademark Office (mailed Jan. 27, 2011).
Gulledge, Office Action for U.S. Appl. No. 11/650,227, 11 pages, United States Patent and Trademark Office (mailed Aug. 5, 2010).
Gulledge, Office Action for U.S. Appl. No. 11/650,227, 12 pages, United States Patent and Trademark Office (mailed Jan. 27, 2011).
Royds, Office Action for U.S. Appl. No. 12/187,937, 17 pages, United States Patent and Trademark Office (mailed Sep. 16, 2010).
Sasan, Office Action for U.S. Appl. No. 12/275,485, 11 pages, United States Patent and Trademark Office (mailed Mar. 2, 2011).
Osinski, Office Action for U.S. Appl. No. 11/650,230, 13 pages, United States Patent and Trademark Office (mailed Jun. 16, 2010).
Osinski, Office Action for U.S. Appl. No. 11/650,230, 13 pages, United States Patent and Trademark Office (mailed Feb. 2, 2010).
Osinski, Office Action for U.S. Appl. No. 11/650,230, 13 pages, United States Patent and Trademark Office (mailed Mar. 1, 2011).
Packard, Office Action for U.S. Appl. No. 11/985,162, 15 pages, United States Patent and Trademark Office (mailed Dec. 20, 2010).
Price, Office Action for U.S. Appl. No. 11/825,212, 9 pages, United States Patent and Trademark Office (mailed Aug. 31, 2010).
Price, Office Action for U.S. Appl. No. 11/825,212, 12 pages, United States Patent and Trademark Office (mailed Mar. 24, 2010).
Scott, Office Action for U.S. Appl. No. 11/980,216, 16 pages, United States Patent and Trademark Office (mailed Dec. 24, 2008).
Scott, Office Action for U.S. Appl. No. 11/980,216, 20 pages, United States Patent and Trademark Office (mailed Jul. 20, 2009).
Scott, Office Action for U.S. Appl. No. 11/980,216, 17 pages, United States Patent and Trademark Office (mailed Jan. 5, 2010).
Scott, Office Action for U.S. Appl. No. 11/980,216, 19 pages, United States Patent and Trademark Office (mailed Jul. 2, 2010).
Barham, Office Action for U.S. Appl. No. 11/974,092, 13 pages, United States Patent and Trademark Office (mailed Mar. 31, 2010).
Brendenberg, "New Concepts in Administration of Drugs in Tablet Form—Formulations and Evaluation of a Sublingual Tablet for Rapid Absorption, and Presentation of an Individualised Dose Administration System", Comprehensive Summaries of Uppsala Dissertations from the Faculty of Pharmacy 287, ACTA Universitatis Upsaliensis Uppsala, Oct. 2003.
Chauvin, M., "Sufentanil Pharmacokinetics in Patients With Cirrhosis", Anesthes Analg, 1989, 68(1):1-4.
Coluzzi P.H., et al., Breakthrough Cancer Pain: A Randomized Trial Comparing Oral Transmucosal Fentanyl Citrate (OTFC) and Morphine Sulfate Immediate Release (MSIR), Pain, 2001, 91(1-2):123-130.
Darwish, "Phamacokinetic Properties of Fentanyl Effervescent Buccal Tablets: A Phase I, Open-Label, Crossover Study of Single-Dose 100, 200, 400 and 800 Microg in Health Adult Volunteers" Clinical Therapies, 2006, 28(5):707-714.
Darwish, M., "Comparison of Equivalent Doses of Fentanyl Buccal Tablets and Arteriovenous Differences in Fentanyl Pharmacokinetics", Clin Pharmacokinet, 2006, 45(8):843-850.
Durfee, Fentanyl Effervescent Buccal Tablets: Enhanced Buccal Absorption, American Journal of Drug Delivery, 2006, 4(1):1-5(5).
Egan, T.D., Multiple Dose Pharmacokinetics of Oral Transmucosal Fentanyl Citrate in Healthy Volunteers, Anesthesiology, 2000, 92:665-673.
Farnsworth, S.T., et al., "Ocular Transmucosal Absorption and Toxicity of Sufentanil in Dogs", Anesth Analg, 1998, 86:138-140.

Gardner-Nix J., "Oral Transmucosal Fentanyl and Sufentanil for Incident Pain", J Pain Symptom Management, Aug. 2001, 22(2):627-630.

Gordon, D.B., Oral Transmucosal Fentanyl Citrate for Cancer Breakthrough Pain: A Review, Oncol Nurs Forum, Nov. 3, 2006, 33(2)257-264.

Haynes, G., "Plasma Sufentantil Concentration After Intranasal Administration to Paediatric Outpatients", Can J. Anaesth, 1993, 40(3):286.

Helmers, et al., 1989, Can J. Anaesth, 1989, 6:494-497.

Jackson K., et al., "Pilot Dose Finding Study of Intranasal Sufentanil for Breakthrough and Incident Cancer-Associated Pain", J Pain Symptom Manage, 2002, 23(6):450-452.

Kunz, K.M., "Severe Episodic Pain: Management With Sublingual Sufentanil", Journal of Pain and Symptom Management, 1993, 8:189-190.

Lennernäs B., "Pharmacokinetics and Tolerability of Different Doses of Fentanyl Following Sublingual Administration of a Rapidly Dissolving Tablet to Cancer Patients: A New Approach to Treatment of Incident Pain", Br J Clin Pharmacol, Feb. 2005, 59(2):249-253.

Lichtor, J.L., "The Relative Potency of Oral Transmucosal Fentanyl Citrate (OTFC) Compared With Intravenous Morphine in the Treatment of Moderate to Severe Postoperative Pain" Anesth Anal, 1999, 89(3):732-738.

Lipworth, et al., Pharmacokinetics, Effacacy and Adverse Efects of Sublingual Salbutamol in Patients with Asthma, European Journal of Clinical Pharmacology, Nov. 1989, 37(6).

Mathieu, N., et al., "Intranasal Sufentanil is Effective for Postoperative analgesia in Adults", Can J Anesth, 2006, 53(1):60-66.

Monk, J.P., "Sufentanil: A Review of Its Pharmacological Properties and Therapeutic Use", Drugs, 1988, 36:286-313.

Okayama, et al, "Bronchodilator Effect of Sublingual Isosorbide Dinitrate in Asthma", Eur J Clin Pharmacol, 1984, 26(2):151-155.

Roy, S.D., "Transdermal Delivery of Narcotic Analgesics: pH, Anatomical, and Subject Influences on Cutaneous Permeability of Fentanyl and Sufentanil", Pharm Res, 1990, 7:842-847.

Sinatra, R.S., "Patient-Controlled Analgesia with Sufentanil: A Comparison of Two Different Methods of Administration", Journal of Clinical Anesthesia, 1996, 8:123-129.

Vercauteren M., "Intranasal Sufentanil for Pre-Operative Sedation", Anaesthesia, 1988, 43(4):270-273.

Weniberg, D.S., Sublingual Absorption of Selected Opioid Analgesics, Clin Parmacol Ther, Sep. 1988, 44(3):335-342.

Wheeler, M., "Uptake Pharmacokinetics of the Fentanyl Oralet in Children Scheduled for Central Venous Access Removal: Implications for the timing of Initiating Painful Procedures", Paediatric Anesthesia, 2002, 12:594-599.

Willens, J.S., "Pharmacodynamics, Pharmacokinetics, and Clinical Uses of Fentanyl, Sufentanil, and Alfentanil", Heart and Lung, 1993, 22:239-251.

Zhang, H., "Oral Mucosal Drug Delivery: Clinical Pharmacokinetics and Therapeutic Applications", Clinical Pharmacokinetics, 2002, 41(9):661-680(20).

Actiq package insert—ACTIQ® is an oral Transmucosal form of fentanyl citrate administered as a lollipop, both indicated for the management of breakthrough cancer pain in patients who are already receiving and who are tolerant to opioid therapy. The Actiq package insert claims that at least 75% of the drug dose is swallowed via the saliva and thus enters the circulation via the GI tract. See p. 4, 2001.

Fentora package insert—100-800mcg dose of fentanyl; buccal absorption with approximately 50% of the total dose absorbed transmucosal and the remaining half of the dose is swallowed and undergoes absorptions via the GI tract. See p. 4, Jun. 2006.

* cited by examiner

SMALL-VOLUME ORAL TRANSMUCOSAL DOSAGE FORMS

CROSS REFERENCE TO OTHER APPLICATIONS

This application claims the priority benefit of U.S. Provisional Application No. 60/756,937, filed Jan. 6, 2006, the disclosure of which is incorporated herein by reference in its entirety.

FIELD OF THE INVENTION

The present invention provides for small-volume oral transmucosal drug delivery dosage forms having various sizes and characteristics, referred to herein as "NanoTabs®" and methods of using the same.

BACKGROUND OF THE TECHNOLOGY

Currently, standard treatment regimens for oral administration of medications for treatment of a number of conditions have clear limitations with regard to both efficacy and toxicity. Routes of administration, formulations and dosage control among other attributes contribute to these limitations.

Reproducible and effective drug delivery technology represents an area of active research and controlled drug delivery systems offer numerous advantages relative to conventional dosage forms, which include improved efficacy, reduced toxicity, as well as improved patient compliance and convenience. This is particularly relevant to the treatment of pain, more specifically: acute, intermittent and breakthrough pain.

Medications based on a variety of routes of administration and the development of new and improved dosage forms for the treatment of a large number of medical conditions, such as pain, is an ongoing process. There remains a need to develop safer drug dosage forms without the fluctuation in efficacious levels that are seen with medications using current commercially available dosage forms. Currently available treatment regimes for treatment of pain often fail to provide patients with sufficient or consistent therapeutic effect, often due to a slow, erratic onset of action and the difficulty in adjusting and controlling doses such that the medical condition is not treated effectively.

U.S. Pat. Nos. 6,974,590, 6,764,696, 6,641,838, 6,585,997, 6,509,036, 6,391,335, 6,350,470, 6,200,604 and US Patent Publication Nos. 20050176790, 20050142197 and 20050142198 describe pharmaceutical combinations of active compounds such as fentanyl and congeners thereof in combination with an effervescent agent used as a penetration enhancer to influence the permeability of the active compound across the buccal, sublingual, and gingival mucosa.

U.S. Pat. Nos. 6,761,910 and 6,759,059 and U.S. Patent Publication No. 20040213855 disclose pharmaceutical compositions for the treatment of acute disorders such as pain by sublingual administration of an essentially water-free, ordered mixture of microparticles with at least one pharmaceutically active agent adhered to the surfaces of the carrier particles by way of a bioadhesion and/or mucoadhesion promoting agent. U.S. Pat. No. 6,759,059 discloses compositions and methods for sublingual administration of fentanyl or a pharmaceutically acceptable salt thereof using a tablet which is approximately 100 mg in size.

U.S. Pat. No. 5,800,832 and U.S. Pat. No. 6,159,498 (Tapolsky, et al.), and U.S. Patent Publication Nos. 20030194420 and 20050013845 disclose a water soluble, biodegradable drug delivery device, e.g., a bilayer film disk having an adhesive layer and a backing layer, both water-soluble, which adheres to mucosal surfaces.

U.S. Pat. Nos. 6,682,716; 6,855,310; 7,070,762 and 7,070,764 and (Rabinowitz, et al.), disclose delivery of an analgesic via the inhalation route using a method which comprises: a) heating a thin layer of analgesic drug on a solid support to form a vapor; and, b) passing air through the heated vapor to produce aerosol particles.

U.S. Pat. No. 6,252,981 (Zhang et al.) discloses oral mucosal drug delivery as an alternative method of systemic drug delivery formulation and method for oral transmucosal delivery of a pharmaceutical. The invention provides a drug formulation comprising a solid pharmaceutical agent in solid solution with a dissolution agent in solid form, yielding a solid solution. The solid solution formulation may be further combined with buffers and other excipients as needed in order to facilitate the drug's manufacturing, storage, administration and delivery through oral mucosal tissue. The formulation can be used with a variety of oral transmucosal delivery dosage forms, such as a tablet, lozenge, lozenge on a stick, chewing gum, and buccal or mucosal patch. See, also Zhang et al, *Clin Pharmacokinet.* 2002; 41(9):661-80.

A number of transmucosal dosage forms for treatment of pain are presently in clinical development, examples of which include a buccal morphine spray and a buccal fentanyl spray (Generex Biotechnology) and an oral, fast-dissolving tablet of fentanyl for sublingual administration (Rapinyl™; Endo Pharmaceuticals). Two transmucosal fentanyl preparations which currently are commercially available are a fentanyl buccal tablet (FENTORA™; Cephalon) and ACTIQ® (Cephalon), an oral transmucosal form of fentanyl citrate administered as a lollipop, both are only indicated for the management of breakthrough cancer pain in patients who are already receiving and who are tolerant to opioid therapy for their underlying persistent cancer pain.

Although various oral drug delivery systems and dosage forms have been described for the treatment of various medical disorders and conditions, there remains a need for improved dosage forms, formulations and treatment regimens for use in the treatment of such medical disorders and conditions, e.g., for treatment of acute and breakthrough pain.

High bioavailability is critical for efficacious treatment with a variety of drugs including opioids, since higher doses of the drug must be packaged in the commercial dosage form to counter the generally poor bioavailability. An example is oxymorphone (Opana®) which has a bioavailability of 10% and therefore must be packaged with nine-fold more drug for the oral tablet versus the equivalent IV dosage form. Especially problematic are drug systems that have large amounts of residual drug left after full usage of the product. An example is IonSys™, which is an inefficient drug delivery system (transdermal) that requires three times the amount of drug packaged into the transdermal patch than is maximally delivered to the patient during regular usage. These inefficient systems, whether oral pills or patches, can be easily abused by injecting the drug intravenously and obtaining full bioavailability of the excess drug. If a given dosage form administered by the intended route of administration provides close to full bioavailability, then abusing the drug by intravenous injection does not provide for increased bioavailability and therefore this formulation may mitigate drug abuse and diversion.

There remains a need for improved dosage forms for oral drug delivery which provide more rapid and consistent onset of action, more consistent plasma concentrations and higher and more consistent bioavailability than currently available dosage forms. The present invention addresses this need.

BRIEF SUMMARY OF THE INVENTION

The present invention provides compositions and methods comprising small volume oral transmucosal drug delivery dosage forms or "NanoTabs®" which contain a predetermined unit dosage of a pharmaceutically active amount of a drug, which may be self-administered, while providing a therapeutic effect and a predictable and safe pharmacokinetic profile.

The small size of the NanoTab® and its placement in the sublingual cavity allow for potent, lipophilic molecules to be absorbed transmucosally with minimal saliva response and minimal swallowing of the drug. This avoidance of gastrointestinal (GI) uptake allows for a more rapid and consistent onset of action, more consistent plasma concentrations and higher bioavailability. This route of administration minimizes drug uptake via the GI route, which is variable and by which significant metabolism of the drug in the stomach and intestines can occur.

The NanoTabs® of the invention have bioadhesive characteristics and can adhere to the oral mucosa, e.g., a sublingual or buccal membrane. Such NanoTabs® can be of the hydrogel-forming or eroding type.

The NanoTabs® of the invention have a mass of less than 100 mg and a volume of less than 100 µl. More specifically, the invention provides NanoTabs® with a mass selected from the group consisting of less than 100 mg, less than 90 mg, less than 80 mg, less than 70 mg, less than 60 mg, less than 50 mg, less than 40 mg, less than 30 mg, less than 20 mg and less than 10 mg and/or a volume selected from the group consisting of less than 100 µl, less than 90 µl, less than 80 µl, less than 70 µl, less than 60 µl less than 50 µl, less than 40 µl, less than 30 µl, less than 20 µl and less than 10 µl.

A NanoTab® of the invention finds utility in oral transmucosal administration of any drug that can be absorbed via the transmucosal route and which suffers from GI and first-pass metabolism and can therefore benefit from this dosage form.

In one aspect, the NanoTabs® of the invention comprise from about 0.25 µg to 99.9 mg, from about 1 µg to 50 mg, or from about 1 µg to 10 mg of the drug.

In one aspect, the invention provides a NanoTab® wherein the drug is an opioid selected from the group consisting of sufentanil, alfentanil, fentanyl, lofentanil, carfentanil, remifentanil, trefentanil, and mirfentanil.

The invention provides NanoTabs® which comprise an opioid drug in an amount selected from the group consisting of from about 0.25 mcg to 200 micrograms (mcg) of sufentanil, from about 2.5 mcg to 100 mcg of sufentanil, from about 0.02 mcg to 5 micrograms per kilogram (mcg/kg) of sufentanil, e.g., about 2.5, 5, 10, or 15 micrograms of sufentanil, from about 10 mcg to 10 mg of alfentanil, from about 2 mcg to 1500 mcg of fentanyl, from about 50 mcg to 1500 mcg of fentanyl, 200 mcg to 1500 mcg of fentanyl, from about 0.25 mcg to 99.9 mg of lofentanil, from about 0.25 mcg to 99.9 mg of carfentanil, from about 0.25 mcg to 99.9 mg of carfentanil, from about 0.25 mcg to 99.9 mg of remifentanil, from about 0.25 mcg to 99.9 mg of trefentanil, from about 0.25 mcg to 99.9 mg of mirfentanil.

The NanoTab® is designed for self-administration by a subject with or without a device, wherein the NanoTab® has a shape selected from the group consisting of a round disc with a flat, concave, or convex face, an ellipsoid shape a spherical shape and a polygon with three or more edges and flat, concave, or convex faces.

A NanoTab® of the invention may be characterized by an erosion time of from 30 seconds up to a 1 minute, 2 minutes, 3 minutes, 4 minutes, 5 minutes, 10 minutes, 15 minutes, 30 minutes, 1 hour, 2 hours, 4 hours, 8 hours or longer.

The bioavailability of a drug following a single or following repeated oral transmucosal administration of a NanoTab® of the invention to a subject is greater than 65%, greater than 75%, greater than 85%, greater than 90% or greater than 94% and has a coefficient of variation of less than 30% or less than 40%.

The NanoTabs® of the invention are further characterized by a $C_{max}$ with a coefficient of variation of less than 30% or 40%; a $T_{max}$ with a coefficient of variation of less than 40%; a plasma half-life of from about 30 minutes to about 4 hours; and a therapeutic time ratio of greater than 0.07 or from about 0.5 to about 2.0 following a single oral transmucosal administration to a subject.

The amount of drug in the NanoTab® that is absorbed via the oral transmucosal route is at least 35%, at least 40%, at least 45%, at least 50%, at least 55%, at least 60%, at least 65%, at least 70%, at least 75%, at least 80%, at least 85%, at least 90%, at least 95%, at least 98% or at least 99% of the total amount of drug in the dosage form.

The invention further provides a method of treating a subject exhibiting a symptomatic medical condition, by administering a NanoTab® of the invention as described herein such that the drug is effective to treat the symptomatic medical condition.

In one embodiment the symptomatic medical condition is pain, e.g., acute pain, breakthrough pain or post-operative pain and the NanoTab® comprises an opioid such as sufentanil or a congener thereof. The invention further provides a method for the treatment of acute pain in a subject, by administering to the subject a therapeutically effective dose of a small-volume drug delivery dosage form or nanotab of the invention using a device or dispenser.

(n=3) compared to intravenous fentanyl administration (n=3) in a healthy, conscious Beagle dog model. Error bars represents±standard error around the mean (SEM).

Figure 7:
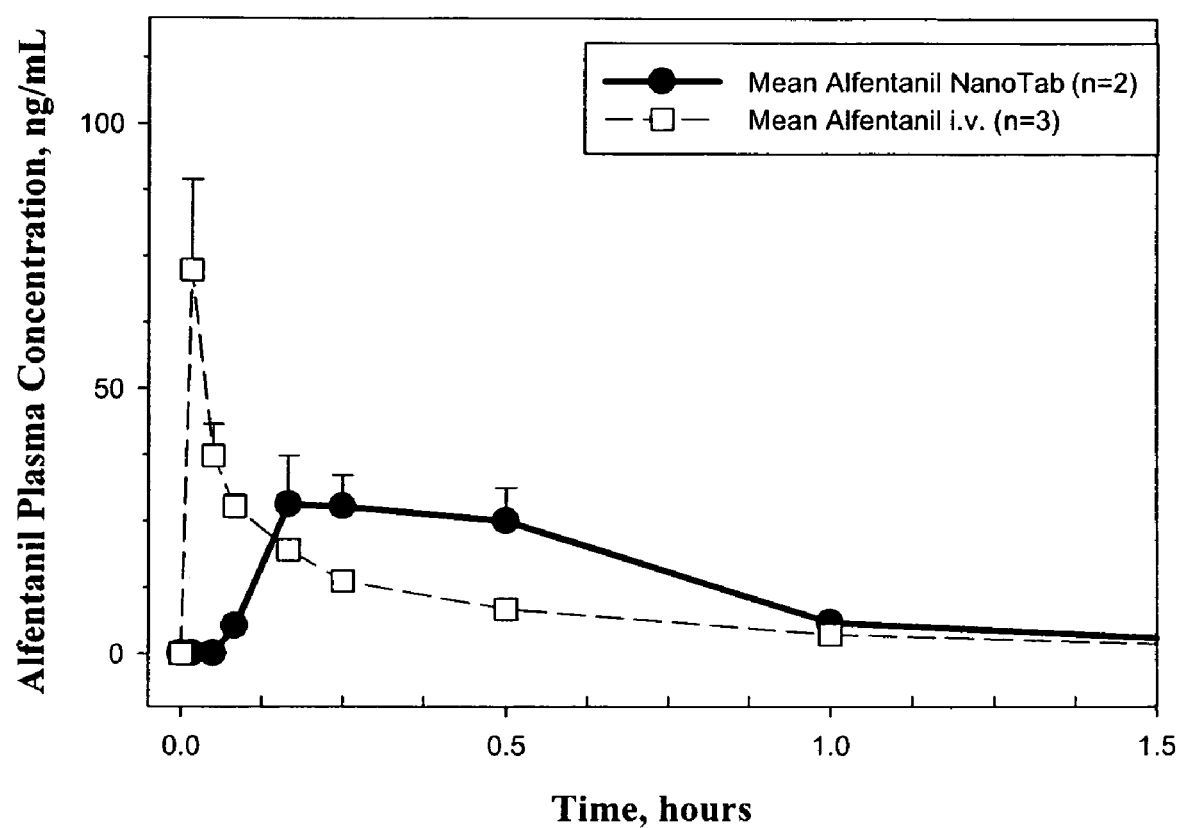

FIG. 7 is a graphic depiction of alfentanil plasma concentrations following sublingual administration of an alfentanil NanoTab® (n=2) compared to intravenous alfentanil administration (n=3) in a healthy, conscious Beagle dog model. Error bars represents±standard error around the mean (SEM).

DETAILED DESCRIPTION

The present invention provides an oral transmucosal dosage form or NanoTab® that provides for high bioavailability, low variability in $T_{max}$, low variability in $C_{max}$ and low variability in AUC. The NanoTabs® of the invention also provide for controlled dissolution, solubility and stability, resulting in controlled release of the drug over time resulting in prolonged plasma levels within the therapeutic window.

The invention is based on a small solid oral transmucosal dosage form or NanoTab®, some embodiments of which adhere to the oral mucosa during the period of drug delivery. The transmucosal dosage form minimizes the saliva response and therefore minimizes delivery of the drug to the GI tract, such that the majority of drug is delivered across the oral mucosa.

The following disclosure describes the NanoTab® dosage forms which constitute the invention. The invention is not limited to the specific dosage forms and methodology or medical conditions described herein, as such may, of course, vary. It is also to be understood that the terminology used herein is for the purpose of describing particular embodiments only, and is not intended to limit the scope of the present invention.

It must be noted that as used herein and in the appended claims, the singular forms "a", "and", and "the" include plural references unless the context clearly dictates otherwise. Thus, for example, reference to "a drug formulation" includes a plurality of such formulations and reference to "a drug delivery device" includes systems comprising drug formulations and devices for containment, storage and delivery of such formulations.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in their entirety for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

DEFINITIONS

The term "NanoTab®" as used herein refers to a small volume dosage form that has a volume of from about 0 ul (microliters) to about 100 ul and a mass of from about 0 mg (milligrams) to about 100 mg. A NanoTab® of the invention may or may not have bioadhesive characteristics and is a dissolvable drug-containing dosage form which may have characteristics of hydrogel-forming or eroding tablets. The nanotab formulation described herein is generally very small. Its volume for example may be from 0.1 to 50 microliters, from 0.5 to 10 microliters, from 1.0 to 25 microliters or more preferably from 3 to 15 microliters. The dimensions of the nanotab may be, for example, from about 0.5 mm to 3 mm in thickness, and from about 1.0 mm to 10 mm in diameter.

The term "formulation" or "drug formulation" or "dosage form" as used herein refers to a physical entity containing at least one therapeutic agent or medication for delivery to a subject. It may be in the form of a lozenge, pill, tablet, capsule, membrane, strip, liquid, patch, film, gel, spray, gum or other form.

The terms "drug", "medication", "pharmacologically active agent" and the like are used interchangeably herein and generally refer to any substance that alters the physiology of an animal. The NanoTabs® of the invention may be used to deliver any drug that may be administered by the oral transmucosal route in an amount amenable to administration via the small size of the NanoTabs®, i.e. 0.25 µg to 99.9 mg, 1 µg to 50 mg or 1 µg to 10 mg.

The term "drug" as used herein with reference to a NanoTabs® of the invention means any "drug", "active agent", "active", "medication" or "therapeutically active agent" that can be effectively administered by the oral transmucosal route.

The term "drug" as applied to the treatment of pain (analgesia) includes sufentanil, sufentanil congeners, such as alfentanil, fentanyl, lofentanil, carfentanil, remifentanil, trefentanil, and mirfentanil, as well as dosage forms comprising one or more therapeutic compounds. Use of "drug" or the phrase "sufentanil or a congener" is not meant to be limiting to use of, or dosage forms comprising only one of these selected opioid compounds. Furthermore, reference to sufentanil alone or to a selected sufentanil congener alone, e.g., reference to "fentanyl," is understood to be only exemplary of the drugs suitable for delivery according to the methods of the invention, and is not meant to be limiting in any way. It will be further understood that a dosage form of the invention may include more than one therapeutic agent, wherein exemplary combinations of therapeutic agents include a combination of two or more opioid analogues, such as sufentanil plus an opioid such as alfentanil, fentanyl, lofentanil, carfentanil, remifentanil, trefentanil, and mirfentanil, or opium alkaloids such as morphine and codeine; semi-synthetic opioids such as heroin and oxycodone; and fully synthetic opioids such as pethidine and methadone, that have structures unrelated to the opium alkaloids, or any other drug that might be disinterred in combination.

The term "congener" as used herein refers to one of many variants or configurations of a common chemical structure.

The term "subject" includes any subject, generally a mammal (e.g., human, canine, feline, equine, bovine, ungulate etc.), in which treatment for a disorder, such as management of pain or anesthetization, is desired.

The term "mucosal membrane" refers generally to any of the mucus-coated biological membranes in the body. Absorption through the mucosal membranes of the oral cavity is of particular interest. Thus, buccal, sublingual, gingival and palatal absorption are specifically contemplated by the present invention. In a preferred embodiment, the penetration enhancers of the present invention are used to improve absorption through those oral tissues which most resemble the skin in their cellular structure, i.e. the gingiva and palate.

The term "transmucosal" delivery of a drug and the like is meant to encompass all forms of delivery across or through a mucosal membrane. In particular, "oral transmucosal" delivery of a drug includes delivery across any tissue of the mouth, pharynx, larynx, trachea, or upper gastrointestinal tract, particularly including the sublingual, gingival and palatal mucosal tissues.

The terms "oral dosage form", "oral transmucosal dosage form" may be used interchangeably herein and refer to a dosage form for use in practicing the present invention.

The oral dosage form is typically a "sublingual dosage form", but in some cases other oral transmucosal routes may be employed. The invention relies upon such oral dosage forms for sustained delivery of drugs across the oral mucosa.

The term "oral transmucosal drug delivery" as used herein refers to a dosage form wherein drug delivery occurs substantially via the transmucosal route and not via swallowing followed by GI absorption. The dosage forms of the current invention are designed to provide for a drug dissolution rate that allows for maximal delivery via the oral mucosa, typically via placement of the dosage form within the sublingual cavity.

As used herein, "sublingual", means literally "under the tongue" and refers to a method of administering substances via the mouth in such a way that the substances are rapidly absorbed via the blood vessels under the tongue rather than via the digestive tract. Owing to the highly vascularized nature of the sublingual mucosal membrane and the reduced number of epithelial cell layers compared to other mucosal membranes, absorption of therapeutic substances occurs rapidly, thus allowing for direct access to the systemic circulation and thus quick onset of action while avoiding all complication of oral administration.

As used herein, the term "hydrogel-forming preparation", means a solid formulation largely devoid of water which upon contact with bodily fluids, and in particular those in the oral mucosa, is capable of absorbing an aqueous solution such as water, in such a way that it swells, while maintaining a structural matrix and forms a hydrated gel in situ. The formation of the gel follows unique disintegration (or erosion) kinetics while allowing for control of the therapeutic drug release over time, which occurs primarily by diffusion.

The term "$T_{max}$" as used herein means the time point of maximum observed plasma concentration.

The term "$C_{max}$" as used herein means the maximum observed plasma concentration.

The term "AUC" as used herein means "area under the curve" in a plot of concentration of drug in plasma versus time. AUC is usually given for the time interval zero to infinity, however, clearly plasma drug concentrations cannot be measured 'to infinity' for a patient so mathematical approaches are used to estimate the AUC from a limited number of concentration measurements. In a practical sense, the AUC (from zero to infinity) represents the total amount of drug absorbed by the body, irrespective of the rate of absorption. This is useful when trying to determine whether two formulations of the same dose release the same dose of drug to the body. The AUC of a transmucosal dosage form compared to that of the same dosage administered intravenously serves as the basis for a measurement of bioavailability.

The term "F" as used herein means "percent bioavailability" and represents the fraction of drug absorbed from the test article as compared to the same drug when administered intravenously. It is calculated from the AUC (0-infinity) of the test article following delivery from the intended route versus the AUC for the same drug after intravenous administration. It is calculated from the equation: F (%)=$AUC_\infty$ (test article)/$AUC_\infty$ (intravenous route/article). This is an important term that establishes the relative fraction of the drug absorbed via the test route (or article) versus the maximum possible amount available via the intravenous route.

The term "Therapeutic Time Ratio" or "TTR" represents the average time that the drug is present at therapeutic levels, defined as time within which the drug plasma concentration is maintained above 50% of $C_{max}$ normalized by the drug's elimination half-life and it is calculated by the formula: TTR= (Time above 50% of $C_{max}$)/(Terminal intravenous elimination half-life of the drug). The last term is obtained from literature data for the drug of interest in the appropriate species.

The term "disintegration" as used herein means the physical process by which a tablet breaks down and pertains to the physical integrity of the tablet alone. This can occur via a number of different ways including breaking into smaller pieces and ultimately, fine and large particulates or, alternatively, eroding from the outside in until the tablet has disappeared.

The term "dissolution" as used herein means the process by which the active ingredient is dissolved from the tablet in the presence of a solvent, in vitro, or physiological fluids in vivo, e.g., saliva, irrespective of the mechanism of release, diffusion of erosion.

The term "swelling ratio" as used herein means the mass ratio of the dosage form after full exposure to water as compared to its mass in the dry state prior to exposure. Swelling ratio (SR) can be defined based on a specified time of exposure to water and expressed as a ratio or a percentage, e.g., SR expressed as a percentage=(Mass after exposure to water− Initial Dry Mass)/(Initial dry Mass)×100.

Alternatively, such a 'swelling ratio' may be defined as the ratio of the volume of a dosage form of the invention following contact with water as compared to the volume of the same dosage form prior contact with water. Swelling ratio (SR) can be defined based on a specified time of exposure to water and expressed as a ratio or a percentage, e.g., SR expressed as a percentage=(Tablet volume after exposure−tablet volume before exposure)/(tablet volume before exposure)×100. When the radial dimensions of such an experiment are well-controlled, the same swelling ratio can be defined in terms of the variable dimension, e.g. thickness, as: SR expressed as a percentage=(Tablet thickness after exposure−tablet thickness before exposure)/(tablet thickness before exposure)×100.

The term "bioadhesion" as used herein refers to adhesion to a biological surface more in general, including mucosal membranes.

The term "therapeutically effective amount" means an amount of a therapeutic agent, or a rate of delivery of a therapeutic agent (e.g., amount over time), effective to facilitate a desired therapeutic effect, such as pain relief. The precise desired therapeutic effect (e.g., the degree of pain relief, and source of the pain relieved, etc.) will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

"Sustained drug delivery" refers to release or administration of a drug from a source (e.g., a drug formulation) over a protracted period of time, for example, over a period of a minute or more. Sustained drug delivery is in effect the opposite of bolus drug delivery.

As used herein, when a drug formulation is said to "adhere" to a surface, such as a mucosal membrane, it is meant that the formulation is in contact with the surface and is retained upon the surface without the application of an external force. Adhesion is not meant to imply any particular degree of sticking or bonding, nor is it meant to imply any degree of permanency.

The term "active agent" or "active" may be used interchangeably herein with the term "drug" and is used herein to refer to any therapeutically active agent.

The term "non-occlusive" is used herein in its broadest sense to refer to not trapping or closing the skin to the atmosphere by means of a patch device, fixed reservoir, application chamber, tape, bandage, sticking plaster, or the like which remains on the skin at the site of application for a prolonged length of time.

The term "mucosal-depot" is used herein in its broadest sense to refer to a reservoir or deposit of active agent within or just beneath the mucosal membrane.

The expression "mucoadhesion" is used herein in to refer to adhesion to mucosal membranes which are covered by mucus, such as those in the oral cavity and is used interchangeably herein with the term "bioadhesion" which refers to adhesion to any biological surface.

The term "drug delivery device" is used interchangeably herein with the term "dispensing device" and means a device that dispenses oral transmucosal dosage forms such as a NanoTab® of the invention, comprising a formulation as further described herein.

Oral Transmucosal Drug Delivery Dosage Forms

The present invention provides oral transmucosal drug delivery dosage forms or NanoTabs®, that produce a reduced saliva response when compared with other oral dosage forms, thus providing high absorption rates of the pharmaceutically active substance provided in the dosage form across the oral mucosa, and reduced uptake via the gastrointestinal tract and therefore offering a more consistent and reproducible means of drug delivery.

The oral dosage form or NanoTab®, is typically a "sublingual dosage form", but in some cases other oral transmucosal routes may be employed. The invention relies upon such oral dosage forms for sustained delivery of drugs across the oral mucosa. The dosage form is a substantially homogeneous composition which comprises one or more active ingredients and may comprise one or more of: mucoadhesives (also referred to herein as "bioadhesives") that provide for adherence to the mucosa of the mouth of a patient; one or more binders that provide binding of the excipients in a single tablet; one or more hydrogel forming excipients; one or more bulking agents; one or more lubricants; one or more absorption enhancers; one or more buffering excipients; as well as coatings and other excipients and factors that modify and control the drug's dissolution time and kinetics or protect the active drug from degradation.

Sublingual delivery is preferred as the sublingual mucosa is more readily permeable to medications than other mucosal areas, such as the buccal mucosa, resulting in more rapid uptake (Shojaei A H, et al. Buccal mucosa as a route for systemic drug delivery: a review. Journal of Pharmacy and Pharmaceutical Sciences. 1:15-30, 1998).

The NanoTabs® of the invention provide for the delivery of a greater percentage (and amount) of drug via the oral mucosa and a corresponding decrease in delivery via the GI tract as compared to traditional oral dosage forms or clinically used oral transmucosal dosage forms.

The preferred site for oral transmucosal drug delivery is the sublingual area, although in certain embodiments it may be advantageous for the dosage form to be placed inside the cheek, or to adhere to the roof of the mouth or the gum.

The dosage forms of the invention are adapted for oral transmucosal (for example sublingual) delivery of a drug and typically have a dissolution time of up to about 60 minutes, in some cases up to about 120 minutes and in other cases as long as several hours.

In general, greater than 30%, greater than 50%, greater than 75% or greater than 95-99% of the drug in the dosage form is absorbed via the oral mucosa.

Application of the drug delivery dosage forms of the present invention is not limited to any particular therapeutic indication. Examples of application of the drug delivery dosage forms of the invention for the treatment of pain are provided herein, however, the NanoTabs® of the invention find utility in treatment of any of a number of medical conditions and disorders, and are not limited to any particular drug or patient population. As such, use of the NanoTabs® of the invention administration of drugs to finds utility in administration of drugs to both pediatric and adult populations and in treatment of human and non-human mammals.

When the NanoTabs® of the invention are used for the treatment of pain, the invention finds utility in administration of drugs to pediatric and adult populations and in treatment of human and non-human mammals, as well as in opioid tolerant and opioid naïve patient populations.

NanoTab® Dosage Form Attributes

In one embodiment, the dosage forms or NanoTabs® of the invention are generally adapted to adhere to the oral mucosa (i.e. are bioadhesive) during the period of drug delivery, and until most or all of the drug has been delivered from the dosage form to the oral mucosa. In other embodiments, the dosage forms or NanoTabs® of the invention are not bioadhesive.

A NanoTab® of the invention has a volume of from about 0 ul (microliters) to about 100 ul, a mass of from about 0 mg (milligrams) to about 100 mg, a thickness of from about 0.1 mm to about 10.0 mm, e.g., from about 0.5 to about 3.0 mm; and a diameter of from about 1.0 mm to about 30.0 mm, from about 1.0 mm to about 10.0 mm, e.g., about 3.0 mm.

More specifically, a NanoTab® of the invention has a mass selected from the group consisting of less than 100 mg, less than 90 mg, less than 80 mg, less than 70 mg, less than 60 mg, less than 50 mg, less than 40 mg, less than 30 mg, less than 20 mg and less than 10 mg.

A NanoTab® of the invention may also have a volume selected from the group consisting of less than 100 µl, less than 90 µl, less than 80 µl, less than 70 µl, less than 60 µl, less than 50 µl, less than 40 µl, less than 30 µl, less than 20 µl and less than 10 µl.

Figure 6:
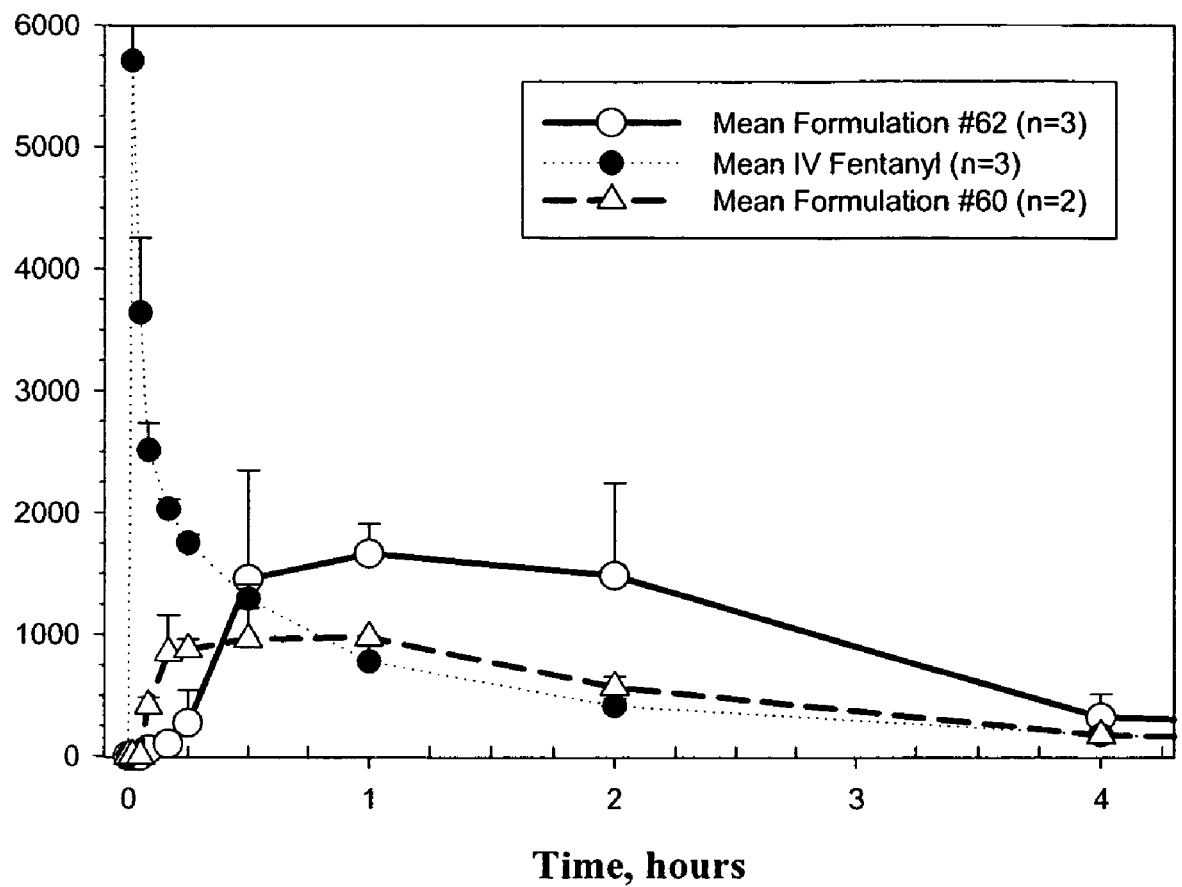
FIG. 6 is a graphic depiction of fentanyl plasma concentrations following sublingual administration of medium disintegrating fentanyl NanoTab® formulation #60 (n=2) and slowly disintegrating fentanyl NanoTab® formulation #62

Shape: The NanoTab® dosage forms of the invention may have essentially any shape that fits the parameters recited herein with respect to NanoTab® dimensions. Exemplary shapes are selected from the group consisting of a round disc with a flat, concave, or convex face, an ellipsoid shape, a spherical shape, a polygon with three or more edges and flat, concave, or convex faces. NanoTab® shapes may be symmetrical or asymmetrical, and may have features or geometries that allow for controlled, convenient, or easy storage, handling, packaging or dosing. FIG. 6 illustrates some of these shapes.

Oral vs. GI uptake: In general, greater than 30%, greater than 50%, greater than 75% or greater than 95-99% of the drug in a NanoTab® of the invention is taken up via the oral mucosa.

In certain embodiments of the invention, the NanoTab® is adapted to deliver 30% or more of the total amount of drug contained in a single drug dosage form to an individual via the oral mucosa. In other embodiments the percentage of the total amount of drug contained in a single drug dosage delivered transmucosally may be greater than 30-40%, 40-50%, 60-70%, 70-80%, 80-90% and preferably greater than 95%.

In exemplary embodiments, at least 35%, 40%, 45%, 50%, 55%, 60%, 65%, 70%, 75%, 80%, 85%, 90%, 95%, 98% or 99%, of the total amount of drug contained in a single drug dosage form is delivered via the oral mucosa.

The delivery of a greater percentage (and amount) of drug via the oral mucosa and the corresponding lack of delivery via the GI tract provides a significant improvement over prior methods of drug delivery.

Reduced Saliva Response: The NanoTab® drug dosage forms of the present invention are designed and adapted to reduce the saliva response, reducing the amount of drug swallowed, and thereby delivering a substantial amount of drug to a subject via the oral mucosa. The NanoTabs® of the invention also provides oral transmucosal dosage forms with improved dissolution profiles over previously described oral or oral transmucosal dosage forms, efficacious delivery of drug via the oral mucosa, and a consistent plasma level within the therapeutic window.

Erosion time: The dosage forms of the invention are designed to provide for an erosion rate that allows for maximal delivery via the oral mucosa, typically via placement of the dosage form in the sublingual location. Erosion times for sublingual administration of the a NanoTab® of the invention is typically from about 30 seconds up to 1 minute, 2 minutes, 3 minutes, 4 minutes, 5 minutes, 10 minutes, 15 minutes, 30 minutes, 1 hour, 2 hours, 4 hours and 8 hours.

Dissolution time: The oral transmucosal formulations of the present invention are typically designed to achieve drug dissolution times of that will vary from 30 seconds up to 1 minute, 2 minutes, 3 minutes, 4 minutes, 5 minutes, 10 minutes, 15 minutes, 30 minutes, 1 hour, 2 hours, 4 hours, 8 hours or longer dependent upon the patient and circumstances of drug administration as well as the intrinsic drug pharmacokinetics. It will be understood that the composition of the oral transmucosal formulations of the present invention may be adjusted to provide for both a range of doses and a range of dissolution times to fit particular clinical situations.

Formulations: A pharmaceutical dosage form of the invention for oral transmucosal delivery may be solid or non-solid. In one preferred embodiment, the dosage from is a solid that turns into a hydrogel following contact with saliva. In another preferred embodiment, the dosage from is a solid that erodes without forming a hydrogel following contact with saliva.

A dosage form of the invention is a substantially homogeneous formulation which comprises 0.01-99% w/w of the active ingredient(s) (drug, medication, etc.) and further comprises one or more of: mucoadhesives (also referred to herein as "bioadhesives") that provide for adherence to the mucosa of the mouth of a patient; one or more binders that provide binding of the excipients in a single tablet; one or more hydrogel forming excipients; one or more bulking agents; one or more lubricants; one or more absorption enhancers; one or more buffering excipients; one or more coatings; one or more controlled release modifiers; and one or more other excipients and factors that modify and control the drug's dissolution or disintegration time and kinetics or protect the active drug from degradation.

Excipients are not limited to those above, and numerous suitable nontoxic pharmaceutically acceptable carriers for use in oral dosage forms can be found in Remington's Pharmaceutical Sciences, 17th Edition, 1985.

The dosage forms of the invention for oral transmucosal drug delivery may include at least one bioadhesive (mucoadhesive) agent or a mixture of several bioadhesives to promote adhesion to the oral mucosa during drug delivery. In addition the bioadhesive or mucoadhesive agents may also be effective in controlling the dosage form erosion time and/or, the drug dissolution kinetics over time when the dosage form is wetted by saliva. In addition, some of the mucoadhesives named in this invention may also serve as binders in the formulation to provide necessary bonding to the dosage form.

Exemplary mucoadhesive or bioadhesive materials are selected from the group consisting of natural, synthetic or biological polymers, lipids, phospholipids, and the like. Examples of natural and/or synthetic polymers include cellulosic derivatives (such as methylcellulose, carboxymethyl cellulose, hydroxyethyl cellulose, hydroxyethylmethyl cellulose, etc), natural gums (such as guar gum, xanthan gum, locust bean gum, karaya gum, veegum etc), polyacrylates (such as carbopol, polycarbophil, etc), alginates, polyoxyethylenes, polyethylene glycols (PEG) of all molecular weights (preferably between 1000 and 40,000 Da, of any chemistry, linear or branched), dextrans of all molecular weights (preferably between 1000 and 40,000 Da of any source), block copolymers, such as those prepared by combinations of lactic & glycolic acid (PLA, PGA, PLGA of various viscosities, molecular weights and lactic-to-glycolic acid ratios) polyethylene glycol-polypropylene glycol block copolymers of any number and combination of repeating units (such as Pluronics, Tektronix or Genapol block copolymers), combination of the above copolymers either physically or chemically linked units (for example PEG-PLA or PEG-PLGA copolymers) mixtures. Preferably the bioadhesive excipient is selected from the group of polyethylene glycols, polyoxyethylenes, polyacrylic acid polymers, such as Carbopols (such as Carbopol 71G, 934P, 971P 974P) and polycarbophils (such as Noveon AA-1, Noveon CA-1, Noveon CA-2), cellulose and its derivatives and most preferably it is polyethylene glycol, carbopol, and/or a cellulosic derivative or a combination thereof.

The mucoadhesive/bioadhesive is typically present at 1-50% w/w, preferably 1-40% w/w or most preferably between 5-30% w/w. A formulation of the invention may contain one or more different bioadhesives in any combination.

The dosage forms of the invention for oral transmucosal drug delivery may also include a binder or mixture of two or more binders which facilitate binding of the excipients into a single dosage form. Exemplary binders are selected from the group consisting of cellulosic derivatives (such as methylcellulose, carboxymethyl cellulose, hydroxyethyl cellulose, hydroxyethylmethyl cellulose, etc), polyacrylates (such as Carbopol, polycarbophil, etc), Povidone (all grades), Polyox of any molecular weight or grade irradiated or not, starch, polyvinylpyrrolidone (PVP), Avicel, and the like.

The binder is typically present at 0.5-60% w/w, preferably 1-30% w/w and most preferably 1.5-15% w/w.

The dosage forms of the invention for oral transmucosal drug delivery may further include one or more hydrogel-forming excipients. Exemplary hydrogel forming excipients are selected from the group consisting of polyethylene glycols and other polymers having an ethylene glycol backbone, whether homopolymers or cross linked heteropolymers, block copolymers using ethylene glycol units, such as polyoxyethylene homopolymers (such as Polyox N10/MW=100, 000 1 Polyox-80/MW=200,000; Polyox 1105/MW=900,000; Polyox-301/MW=4,000,000; Polyox-303/MW=7,000,000, Polyox WSR-N-60K, all of which are tradenames of Union Carbide), hydroxypropylmethylcellulose (HPMC) of all molecular weights and grades (such as Metolose 90SH50000, Metolose 90SH30000, all of which are tradenames of Shin-Etsu Chemical company), Poloxamers (such as Lutrol F-68, Lutrol F-127, F-105 etc, all tradenames of BASF Chemicals), Genapol, polyethylene glycols (PEG, such as PEG-1500, PEG-3500, PEG-4000, PEG-6000, PEG-8000, PEG-12000, PEG-20,000, etc.), natural gums (Xanthan gum, Locust bean gum, etc) and cellulose derivatives (HC, HMC, HMPC, HPC, CP, CMC), polyacrylic acid-based polymers either as free or cross-linked and combinations thereof, biodegradable polymers such as poly lactic acids, polyglycolic acids and any combination thereof, whether a physical blend or cross-linked. In an embodiment, the hydrogel components may be cross-linked. The hydrogel forming excipient(s) are typically present at 0.1-70% w/w, preferably 1-50% w/w or most preferably 1-30% w/w.

The dosage forms of the invention for oral transmucosal drug delivery may also include at least one controlled release modifier which is a substance that upon tablet hydration will preferentially adhere to the drug molecules and thus reduce the rate of its diffusion from the oral dosage form. Such excipients may also reduce the rate of water uptake by the formulation and thus enable a more prolonged drug dissolution and release from the tablet. In one embodiment, such controlled release modifiers are capable of binding molecularly to the active via physical (and therefore reversible) interactions, thus increasing the effective molecular weight of the active and thus further modifying their permeation (diffusion) characteristics through the epithelial and basal membranes of the sublingual mucosa. Such binding is reversible in nature and does not involve any chemical modifications of the active, thus it does not affect in any way its pharmacological action. In another preferred embodiment, such controlled release modifiers upon hydration may form concrete structures that may entrap spontaneously the active and thus further prolong its action. Exemplary controlled release modifiers are selected from the group consisting of lipids, phospholipids, sterols, surfactants, polymers and salts. In general the selected excipient(s) are lipophilic and capable of naturally complexing to the hydrophobic or lipophilic drugs. The degree of association of the release modifier and the drug can be varied by altering the modifier-to-drug ratio in the formulation. In addition, such interaction may be appropriately enhanced by the appropriate combination of the release modifier with the active drug in the manufacturing process. Alternatively, the controlled release modifier may be a charged polymer either synthetic or biopolymer bearing a net charge, either positive or negative, and which is capable of binding to the active via electrostatic interactions thus modifying both its diffusion through the tablet and/or the kinetics of its permeation through the mucosal surface. Similarly to the other compounds mentioned above, such interaction is reversible and does not involve permanent chemical bonds with the active drug.

A controlled release modifier may typically be present at 0-80% w/w, preferably 1-20% w/w, most preferably 1-10% w/w.

The dosage forms of the invention for oral transmucosal drug delivery also typically include at least one filler (bulking agent). Exemplary bulking agents are selected from the group consisting of lactose USP, Starch 1500, mannitol, sorbitol, malitol or other non-reducing sugars; microcrystalline cellulose (e.g., Avicel), dibasic calcium phosphate dehydrate, sucrose, and mixtures thereof. The filler/bulking agent is typically present at 20-99% w/w, preferably 40-80% w/w.

The dosage forms of the invention for oral transmucosal drug delivery may also include at least one lubricant. Exemplary lubricants are selected from the group consisting of magnesium stearate, stearic acid, calcium stearate, talc, stearowet and sterotex and the like. The lubricant is typically present at 0.01-8% w/w, preferably between 0.1-3% w/w.

The formulation may also contain flavors or sweeteners and colorants such as aspartame, mannitol, lactose, sucrose, other artificial sweeteners; ferric oxides and FD&C lakes.

The formulation may also contain additives to help stabilize the drug substance from chemical of physical degradation. Such degradation reactions may include oxidation, hydrolysis, aggregation, deamidation, etc. Appropriate excipients that can stabilize the drug substance may include anti-oxidants, anti-hydrolytic agents, aggregation-blockers etc. Anti-oxidants may include BHT, BHA, vitamins, citric acid, EDTA etc. Aggregation blockers may include surfactants, amino-acids, etc.

The formulation may also contain surfactants to increase wetting of the tablet, especially if faster release kinetics are desired, which could result in faster initiation of mucoadhesion. Such surfactants should be from 0.01 to 3% weight percent of the composition. Exemplary surfactants are selected from the group consisting of ionic (sodium lauryl sulfate, etc), non-ionic such as polysorbates (Tween and Span surfactant series), bile salts (such as sodium taurocholate, sodium taurodeoxycholate, sodium glycodeoxycholate, sodium glycocholate, etc), various alkyl glycosides, and mixtures thereof.

A dosage form of the invention may additionally comprise one or more excipients that may affect both tablet disintegration kinetics and drug release from the tablet, and thus pharmacokinetics. Such additives are disintegrants such as those known to those skilled in the art and may be selected from a group consisting of starch, carboxy-methycellulose type or crosslinked Polyvinyl Pyrrolidone (such as cross-povidone, PVP-XL), alginates, cellulose-based disintegrants (such as purified cellulose, methylcellulose, crosslinked sodium carboxy methylcellulose (Ac-Di-Sol) and carboxy methyl cellulose), microcrystalline cellulose (such as Avicel), ion exchange resins (such as Ambrelite IPR 88), gums (such as agar, locust bean, karaya, Pectin and tragacanth), guar gums, gum Karaya, chitin and chitosan, Smecta, gellan gum, Isapghula Husk, Polacrillin Potassium (Tulsion$^{339}$), gas-evolving disintegrants (such as citric acid and tartaric acid along with the sodium bicarbonate, sodium carbonate, potassium bicarbonate or calcium carbonate), sodium starch glycolate (such as Explotab and Primogel), Addition of such additives facilitates the fast breakup or disintegration of the dosage form into smaller particles that dissolve more rapidly than in the absence of disintegrants. An additional benefit of inclusion of such disintegrants in the dosage forms of the present invention which contain the bioadhesive materials described herein, is that the smaller, drug-containing particles formed upon disintegration have, by virtue of the highly increased surface area of contact with the oral mucosa, superior bioadhesive properties. In addition, the increased surface area may further facilitate the fast release of the active substance and thus further accelerate drug absorption and attainment of the required therapeutic levels systemically. However, as described above, such disintegrants are used at a low level in the solid dosage form, typically 1-20% w/w relative to the total weight of the dosage unit.

In one aspect of the invention, the dosage forms comprise at least one biodegradable polymer of any type useful for extended drug release. Exemplary polymer compositions include polyanhydrides and co-polymers of lactic acid and glycolic acid, poly(dl-lactide-co-glycolide) (PLGA), poly (lactic acid) (PLA), poly(glycolic acid) (PGA), polyorthoesters, proteins, and polysaccharides.

The dosage forms of the invention for oral transmucosal drug delivery may further include one or more absorption enhancers, one or more buffering excipients and/or one or more coatings to improve, for example, hardness and friability.

In another aspect of the invention, the active ingredient can be chemically modified to significantly modify the pharmacokinetics in plasma. This may be accomplished for example by conjugation with polyethylene glycol (PEG), including site-specific PEGylation. PEGylation, which may improve drug performance by optimizing pharmacokinetics, decreasing immunogenicity and dosing frequency.

TheNanoTabs® of the present invention are provided in a number of dosage forms that vary according to the nature and amount of active ingredients while maintaining the features of the NanoTabs® of the invention for controlled dissolution in the oral cavity. Thus, a greater percentage of drug absorption takes place via the oral mucosal route and not the GI route and resulting in controlled release of the drug over time resulting in prolonged plasma levels within the therapeutic window. The NanoTabs® of the present invention further provide for high bioavailability, low variability in $T_{max}$, low variability in $C_{max}$ and low variability in AUC.

In one aspect of the invention, when a homogeneous dosage form comprising a formulation according to the present invention is placed in the sublingual cavity, preferably under the tongue on either side of the frenulum linguae, it adheres upon contact. As the dosage form is exposed to the moisture of the sublingual space the dosage form absorbs water, resulting in the formation of a hydrogel network, comprising micro- and macro-pores (or channels). Hydration of the drug affects dissolution and subsequent diffusion through the porous network of the dosage form. Hydrogel dosage forms of the invention are characterized by swelling to at least 110% of the initial volume upon contact with an aqueous solution.

Hydrogel formation in the dosage forms of the invention takes place in the presence of certain hydrogel-enabling excipients that have the capacity to absorb water and form gels. Such excipients include Polyox of all grades, polyethylene glycols (of all grades), PEG-based copolymers, whether homopolymers or heteropolymers (such as Poloxamer, etc), Dextran, HPMC, starch, etc, as detailed above. In addition, any combination of such excipients may favor hydrogel formation upon contact with bodily fluids. Further, combinations of such hydrogel forming excipients with excipients that do not favor gel formation (i.e., don't have such a capacity to swell), e.g., Carbopol, certain celluloses, and the like will result in formation of hydrogel structures, albeit with modified properties.

In another aspect of the invention, dosage forms referred to herein as "eroding-type" dosage forms are provided. Such "eroding-type" dosage forms, although they may absorb significant amounts of water (depending on their composition) they do not have the same capacity of swelling and consequently they do not form gels as described for the hydrogel type formulations defined above. These "eroding-type" formulations adhere to the sublingual cavity upon contact, similar to the hydrogel formulation. However, in contrast to the hydrogels, they follow a surface-erosion mechanism without prior formation of a hydrogel. As an "eroding-type" dosage form is exposed to the moisture of the sublingual space, the surface of the tablet hydrates and erodes; the subsequent layers become hydrated and erode, thus resulting in a continuous reduction in the size of the tablet.

Such eroding-type dosage forms are typically characterized by a lack of inclusion of hydrogel-forming excipients. However, it will be understood that the percentage weight to weight (w/w) composition of the various components of the dosage form will impact the mechanism of erosion. For example, small amounts of particular hydrogel-enabling excipients may not induce formation of a hydrogel and as such, some hydrogel-enabling excipients may be included in eroding formulations without changing their erosion-based disintegration mechanism. It is both the combination of excipients and their percent weight composition that gives a hydrogel its capacity to swell and maintain a structural matrix upon contact with an aqueous solution. In other words, in general, inclusion of a hydrogel-enabling excipient in a given formulation will not necessarily make the dosage form "swell" as is typical of a hydrogel formulation. A dosage form which becomes a hydrogel swells to at least 110% of its initial volume upon contact with an aqueous fluid.

Pharmacokinetics (PK)

The uptake of transmucosal medications via NanoTabs® results in a more consistent drug delivery between individual dosages and individual patients as compared to that of currently available oral transmucosal dosage forms for which a large fraction of drug uptake occurs via the GI route.

The dosage forms of the present invention are designed to work effectively in the unique environment of the oral cavity such that a limited amount of fluid, a relatively short period of time for drug dissolution, and pH levels within the oral cavity do not adversely affect absorption of the drug. The dosage forms are also designed to improve dissolution, solubility, and stability of the drug. The advantages of the present invention include the ability to provide higher levels of drug absorption via oral transmucosal delivery, and consistent dose-to-effect times, making the present formulation a significant improvement for the treatment of acute or breakthrough pain.

The oral transmucosal dosage forms of the present invention are designed to avoid the high peak plasma levels of intravenous dosage forms by utilizing the sublingual mucosa and by independently controlling both tablet disintegration (or erosion) and drug dissolution and release from the tablet over time to provide a safer delivery profile. The oral transmucosal dosage forms of the present invention provide individual, repetitive doses that include a defined amount of the active agent, thereby allowing the patient to accurately titrate the amount of drug delivered and to adjust the amount as appropriate in a safe and effective manner.

An advantage of the controlled-release oral transmucosal dosage forms described in this invention is that they exhibit high consistent bioavailability and can maintain the plasma drug concentration within a targeted therapeutic window with significantly lower variability for a longer duration than currently available dosage forms, whether solid dosage forms or IV dosage forms. The high peak plasma levels typically observed for IV dosage forms are blunted following administration of a NanoTab® of the invention, which are characterized by controlled release of the drug over 1 to 60 minutes or longer. In addition, a rapid decline in plasma levels is avoided since the drug is continually crossing from the oral cavity into the bloodstream during the length of time of dissolution of the tablet or longer, thus providing plasma pharmacokinetics with an extended plateau phase as compared to the IV route of administration. Further, the dosage forms of this invention may improve treatment safety by minimizing the potentially deleterious side effects due to the relative reduction of the peaks and troughs in the plasma drug pharmacokinetics, which compromise treatment safety and is typical of currently available dosage forms.

Advantages of a solid sublingual dosage form over various liquid forms for either sublingual or intranasal administration of opioids include the controlled local release of the solid dosage form and the avoidance of swallowed liquid drug via either the nasal or oral route. Published pharmacokinetic data on intranasal sufentanil liquid administration (15 mcg) in humans demonstrates a bioavailability of 78% (Helmers et al. Comparison of intravenous and intranasal sufentanil absorption and sedation. Canadian Journal of Anaesthesia 36:494-497, 1989). Sublingual liquid sufentanil administration (5 mcg) in Beagle dogs (see Example 4 below) resulted in a bioavailability of 40%. The aforementioned bioavailability data are less than the 91% average bioavailability that was obtained in human volunteers using sufentanil administered sublingually in the form of a NanoTab® of the invention (see Example 1 below).

Due to the small size of the NanoTabs®, repeated placement in the sublingual cavity over a duration of time is possible. Minimal saliva production and minimal physical discomfort occurs due to the small size, which allows for repetitive titration over days to weeks to months. Given the lipid profile of the sublingual cavity, this route, for certain drugs, also allows for slower release into the plasma which may be due to utilization of a "depot" effect that further stabilizes plasma levels compared to buccal delivery.

The oral transmucosal dosage forms of the invention are designed to fit comfortably under the tongue such that the drug form disintegrates sufficiently slowly to avoid the immediate peak plasma levels followed by significant drop off seen in prior art formulations such as described in U.S. Pat. No. 6,759,059 (Rapinyl), wherein fentanyl was administered via tablets containing 400 mcg of fentanyl which resulted in a peak plasma level of 2.5 ng/ml followed by an immediate drop in plasma level. Fentora (fentanyl buccal tablet) also suffers from a lack of a plateau phase but rather has a steep incline up to the $C_{max}$ followed by a significant drop-off in plasma levels (Fentora package insert).

Tests for Evaluation of NanoTabs®

Prior to the human and animal studies of sublingual NanoTabs® performed in support of the present invention and described below in the specification and in Examples 1-6 in humans and animals, the inventors were not aware of any published pharmacokinetic data obtained in animals or humans from the use of sublingual sufentanil in any dosage form or of sublingual alfentanil in any dosage form.

In Vivo Evaluation.

Human Studies

A human clinical study was performed using healthy volunteers. The study which is detailed in Example 1 below was performed with 12 subjects (6 men and 6 women) using sublingual sufentanil NanoTabs® containing either 2.5 µg, 5 µg or 10 µg of sufentanil base corresponding to 3.7 µg, 7.5 µg or 15 µg of sufentanil citrate, respectively (see Table 1). All excipients were inactive and have GRAS ("generally recognized as safe") status.

Sufentanil NanoTabs® designed for sublingual use were compared to IV sufentanil, administered through an IV catheter as a continuous infusion over 10 minutes. Plasma samples were drawn from a different IV catheter at a remote location. The assay demonstrated good inter-day precision and accuracy at the high, medium and low quality control sample concentrations.

The NanoTabs® for this study eroded over a period of 10-30 minutes in all subjects. After placement of each sufentanil sublingual NanoTab® in the sublingual cavity of the 12 healthy volunteers, a remarkably consistent pharmacokinetic profile was obtained (see FIG. 2 and Table 2). The bioavailability compared to IV administration for single administration of all three dosages averaged 91%, which is far superior to that measured for commercially available fentanyl transmucosal preparations, Actiq and Fentora (47% and 65%, respectively—Fentora package insert). Although this high bioavailability could be due to a number of factors, it is likely that the lack of saliva produced by the small NanoTab® size significantly limits the swallowing of the drug and avoids the low bioavailability typical of drug absorption via the GI route. Both Fentora and Actiq package inserts claim at least 50% and 75% of the drug dose, respectively, is swallowed via the saliva, and both exhibit lower bioavailability than the NanoTabs® of the invention. The NanoTabs® used in this clinical trial had a volume of approximately 5 microliters (mass of 5.5 mg), a small fraction of the size of Actiq or Fentora lozenges. The dog studies described in Example 4 and discussed above demonstrate that sufentanil has very poor GI bioavailability (12%), therefore, given the high bioavailability of the sufentanil NanoTabs®, wherein drug is administered by the oral transmucosal route, the data supports the conclusion that greater than 75% of the drug is absorbed transmucosally. Therefore, less than 25% of the drug is swallowed, which is a much lower percentage than is swallowed with Fentora or Actiq.

Importantly, this high bioavailability is also linked to high consistency of total drug delivered to the patient. For example, the total plasma drug area under the curve (AUC 0-infinity) for sufentanil NanoTabs® 10 mcg was 0.0705±0.0194 hr*ng/ml (mean±standard deviation (SD)). This SD is only 27.5% of the total AUC. Coefficient of variation (CV) is a term to describe the percent SD of the mean. The coefficient of variation for Fentora AUC is 45% and for Actiq AUC is 41% (Fentora package insert). Therefore the total dose delivered to the patient/subject is not only more bioavailable for the sufentanil NanoTabs® but it is more consistently the same from patient to patient.

The sufentanil sublingual NanoTabs® are also superior in terms of consistent drug plasma levels early after administration. The $C_{max}$ obtained with the 10 mcg sufentanil NanoTab® was 27.5±7.7 pg/ml. The coefficient of variation of the $C_{max}$ therefore is only 28%. The $C_{max}$ for Fentora and Actiq suffer from variability of GI uptake of drug. Fentora reports a $C_{max}$ of 1.02±0.42 ng/ml, therefore the coefficient of variation of the $C_{max}$ is 41%. The range of coefficients of variation for the various doses of Fentora is from 41% to 56% (package insert). Actiq coefficient of variation of $C_{max}$ is reported as 33% (Fentora package insert).

In addition to superior bioavailability and consistency in plasma concentrations, the time to $C_{max}$, also referred to as $T_{max}$, is important since quick and consistent onset of pain relief is important in the treatment of acute pain. The $T_{max}$ for sufentanil NanoTabs® 10 mcg was 40.8±13.2 minutes (range 19.8-60 minutes). The reported average $T_{max}$ for Fentora is 46.8 with a range of 20-240 minutes. The $T_{max}$ for Actiq is 90.8 minutes, range 35-240 minutes (Fentora package insert). Therefore the consistency in onset of analgesia for sufentanil NanoTabs® is markedly improved over Fentora and Actiq, with a 400% decrease in the slowest onset of $T_{max}$.

Important in the treatment of acute pain, especially acute breakthrough pain, is a consistent and relatively short half-life of the drug. The plasma elimination half-life of the 10 mcg sufentanil NanoTab® was 1.71±0.4 hours, which allows the drug to be titratable for various levels of pain. If the breakthrough pain event lasts longer than 1.5 hours then the patient can dose with another NanoTab®. The plasma elimination half-life of Actiq and Fentora are 3.2 hours and 2.63 hours, respectively, for the lowest doses. The half-lives for the higher doses increase substantially for these drugs, thereby limiting the titratability of these drugs.

Although still in development, published data allows us to compare the sufentanil NanoTab® pharmacokinetic data provided herein to that of Rapinyl, a fentanyl sublingual fast-dissolve lozenge. As previously mentioned, the observed bioavailability for the sufentanil NanoTabs® of the invention averaged 91% as compared to the published bioavailability for Rapinyl which is approximately 70% (Bredenberg, New Concepts in Administration of Drugs in Tablet Form, Acta Universitatis Upsaliensis, Uppsala, 2003). The coefficient of variation of the AUC (0-infinity) for Rapinyl ranges from 25-42% depending on dose, whereas our value is 27.5% for the 10 mcg sufentanil NanoTabs®. Our high bioavailability would suggest that regardless of dose, the sufentanil Nano-Tabs® will have a consistently low variation of AUC, whereas this is not true for Rapinyl. In fact, our AUC coefficient of variation for all three of the doses of sufentanil NanoTabs® averaged 28.6%, demonstrating that this low variation is not dependent on dose.

The coefficient of variation of the $C_{max}$ for Rapinyl varies from 34-58% depending on dose. As shown by the data presented herein, the 10 mcg sufentanil NanoTab® dose exhibited a $C_{max}$ variation of only 28%, and the average coefficient of variation of the $C_{max}$ for all three dosage strengths of the NanoTabs® (2, 5, and 10 mcg) was 29.4%, indicating minimal variability depending on dose. Similarly, the coefficient of variation for $T_{max}$ with Rapinyl ranges from 43-54% depending on dose, whereas for our sufentanil NanoTabs®, this coefficient of variation for $T_{max}$ averages only 29% over all three dosage strengths. This consistent onset of action achieved with sufentanil NanoTabs® allows a safer redosing window when compared to any of the three comparator drugs, since rising plasma levels are contained to a shorter period.

Additionally, as with Fentora and Actiq, Rapinyl demonstrates a longer plasma elimination half-life (5.4-6.3 hours, depending on dose) than sufentanil NanoTabs®. The plasma elimination half-life of sufentanil NanoTabs® ranged from 1.5-2 hours following a single oral transmucosal administration in humans (Table 2), which allows for more titratability and avoids overdosing. As will be understood by those of skill in the art, the half-life described herein for the exemplified NanoTabs® may be adjusted by modification of the component and relative amounts of the excipients in the formulation used to make a given NanoTab®. The ability to titrate to higher plasma levels by administering repetitive doses of the sublingual sufentanil NanoTabs® was also tested in this human study. Repeat dosing of 5 mcg NanoTabs® every 10 minutes for four dosings resulted in a bioavailability of 96%, indicating that repetitive dosing to achieve higher plasma levels while still maintaining high bioavailability is possible. Whether treating post-operative pain or cancer break-through pain, being able to efficiently titrate to an individual's own level of pain relief is important.

Plateau Plasma Levels

Another aspect of the PK curves generated by sublingual sufentanil NanoTabs® is the plateau phase, which allows for a period of consistent plasma levels, which is important for both safety and efficacy. Compared to either IV bolus administration (see Animal Studies Examples 2-6) or the 10 minute IV infusion in our human study (Example 1 and FIG. 2), the PK profile for the sufentanil NanoTabs® is clearly safer. Rapid, high $C_{max}$ plasma levels are avoided. Given the ability of opioids to produce respiratory depression, avoiding these high peaks in the PK profile is advantageous.

An important mathematical ratio that demonstrates the prolonged plateau phase of the measured blood plasma levels of sufentanil following administration of a NanoTab® is the time spent above 50% of $C_{max}$ divided by the known IV terminal elimination half-life of the drug:

$$\text{Therapeutic Time Ratio} = \frac{\text{Time of offset of } C_{max}/2 - \text{Time of onset of } C_{max}/2}{\text{IV Elimination Half-Life of the Drug}}$$

The elimination half-life is an intrinsic property of the molecule and is measured most reliably using the IV route to avoid contamination from continued uptake of drug from the sublingual route. The IV elimination half-life for 5 mcg of sufentanil in our human study was 71.4 minutes due to the detection limits of the assay at these low doses. The published IV elimination half-life for sufentanil at much higher doses is 148 minutes, due to detection of both the rapid alpha-elimination mechanism of redistribution and the longer beta phase of elimination via metabolism and excretion. This published elimination half-life is more accurate and more appropriate to use in the above equation. The time spent above 50% of $C_{max}$ on average for the 12 volunteers for the 2.5, 5 and 10 mcg dosage strengths was 110 minutes, 111 minutes and 106 minutes, respectively. Therefore, the Therapeutic Time Ratio for these specific sufentanil NanoTabs® ranged from 0.72-0.75. As the formulation of the NanoTabs® is varied, erosion time of the NanoTab® will be either decreased or increased, and one might see a range of Therapeutic Time Ratios from approximately 0.2-2.0 for sufentanil. In fact, any oral transmucosal dosage form of the invention for sufentanil may exhibit Therapeutic Time Ratios in this range and therefore we are not limiting this claim to specific NanoTab® attributes.

This Therapeutic Time Ratio is a measure of how successfully short-acting drugs are formulated to produce an increase in therapeutic time and increase safety by avoiding high peak plasma $C_{max}$ concentrations. For example, as a comparison, the sufentanil IV arm of the human study demonstrated a Therapeutic Time Ratio of 10 min/148 min=0.067. This low ratio value for the IV arm, therefore, is a measure of the high peak produced by IV infusion of sufentanil and demonstrates that this formulation does not produce a significant plateau phase. There is a 10-fold higher Therapeutic Time Ratio for the sufentanil formulations listed in Table 1 (the dosages used in the human study) versus IV sufentanil, indicating a prolonged therapeutic plateau profile for these NanoTab® formulations.

Animal Studies

A series of studies in awake, alert Beagle dogs was performed to more fully elucidate the properties of NanoTabs® using various drugs and NanoTab® formulations. Comparisons of oral transmucosal drug delivery using NanoTabs® of the invention relative to liquid sublingual administration as well as swallowed NanoTabs® were made to evaluate various attributes of the NanoTabs®. The results support our claim that the small, bioadhesive NanoTabs® of the invention are well tolerated sublingually (as demonstrated by use in awake dogs) and result in higher bioavailability and more consistent pharmacokinetic data than other oral transmucosal dosage forms, including instilled liquids.

The first Beagle dog study was carried out to compare a sublingual 5 mcg sufentanil NanoTab® to IV sufentanil as described more fully in Example 2 below. A total of three Beagle dogs were studied and the results are graphed in FIG. 3 and tabulated in Table 3. The bioavailability of the sublingual sufentanil NanoTabs® was 75% compared to IV. Therefore, similar to the human data, this bioavailability data in dogs confirms the superior attributes of the NanoTab® over larger dosage forms. Furthermore, similar to the human data, the coefficient of variation for the AUC was low, 14%, compared to the variation of other commercial transmucosal dosage forms. The Therapeutic Time Ratio of the sublingual sufentanil NanoTab® is 0.28 whereas the Ratio for IV sufentanil is 0.05 (using the published IV elimination half-life of sufentanil in dogs of 139 minutes). Therefore, similar to humans, the 5 mcg NanoTab® formulation in Table 1 resulted in a much higher Therapeutic Time Ratio (5.6-fold) compared to IV sufentanil in dogs.

Additional studies determined the effect of varying the formulation of the NanoTabs® on the pharmacokinetic profile. This study is explained more fully in Example 3 below. By prolonging the erosion time of the NanoTab®, the plasma half-life was extended from 33 minutes for the medium disintegrating NanoTab® (in Example 2) to 205 minutes. The Therapeutic Time Ratio was increased from 0.28 to 1.13 for the slow disintegrating NanoTab®. This study illustrates the flexibility of the NanoTab®, based on excipient selection, to alter the PK of the drug. This flexibility is possible due to the small size of the NanoTab®, which allows either short or prolonged contact time with the sublingual mucosa without dislodging or creating excess saliva which would prematurely wash the drug into the GI tract.

Another study in Beagle dogs was performed to evaluate the advantages of the sublingual NanoTab® dosage form over liquid administration sublingually. This study is described more fully in Example 4 below. The results indicate that although delivery of sufentanil (5 mcg) in an instilled liquid dosage form to the sublingual cavity results in rapid $T_{max}$, this method of drug administration results in very low bioavailability (40%) compared to sublingual sufentanil NanoTabs® (75%). This is probably due to swallowing of the liquid drug. Moreover, the AUC is extremely variable, as shown by the high coefficient of variation (82%). The $C_{max}$ is also highly variable with this method of drug administration, demonstrating a coefficient of variation of 72%. The Therapeutic Time Ratio for instilled liquid sufentanil sublingually was calculated as 0.06, very similar to the IV sufentanil arm for this study which demonstrated a Ratio of 0.03. Therefore, this instilled sublingual liquid profile does not provide the advantageous therapeutic plateau observed with the sublingual NanoTabs®. These findings support that the high sublingual bioavailability observed from the bioadhesive formulations claimed in this application (NanoTabs®) is not intrinsic to the molecule but rather it is a direct result of the unique design of the dosage form and its formulation. The NanoTabs®'s strong adherence in the sublingual cavity minimizes the variability in the surface area available for absorption, as is the case of a liquid solution, thus improving delivery of the molecule to the systemic circulation. In addition, owing to its unique design and small dimensions, the NanoTab® does not elicit significant saliva production, thus reducing the potential for ingestion of the released drug. Both factors contribute to the higher and more uniform drug absorption from the sublingual cavity.

An additional part of this study in Example 4 was the determination of the bioavailability of swallowed sufentanil NanoTabs®. Since there is little to no data on sufentanil GI bioavailability in the literature, it was important to further evaluate the low bioavailability of this route of administration to further support the observation that drug from the sublingual use of NanoTabs® could not be swallowed and maintain a high bioavailability. As indicated by the PK analysis data in Table 7, oral bioavailability of sufentanil from the swallowed NanoTabs® is very low, approximately 12%. In addition, as predicted from the known erratic GI uptake of fentanyl congeners, the swallowed NanoTabs® demonstrated extremely high variability both in the amount of drug absorbed (AUC) and the pharmacokinetics of absorption ($C_{max}$, $T_{max}$) as shown in Table 7. These data support the conclusion that the bioadhesive sublingual NanoTabs® of the invention strongly adhere in the sublingual cavity in such a manner that they don't dislodge, thus avoiding oral ingestion and avoiding the high variability of plasma levels which is typical when drug is absorbed via the GI route.

Additional studies evaluating other drugs, such as fentanyl and alfentanil, formulated into NanoTabs® were also performed in Beagle dogs and are more fully described in Examples 5 and 6 below. These studies support the claim that the NanoTab® can effectively deliver a variety of drugs sublingually with high bioavailability. Fentanyl NanoTabs® were created in both a medium and a slow disintegrating NanoTab® formulations (see Tables 8 and 9). Both formulations resulted in high bioavailability (95% and 90%, respectively), much higher than with any other fentanyl oral transmucosal formulation patented to date. The coefficient of variation of the AUCs was extremely low (10.5% and 4.5%, respectively). These data support the attributes of the NanoTab® and demonstrate that these attributes are not limited to a specific drug. The slower disintegrating fentanyl NanoTab® displayed a slower $T_{max}$ (50 minutes vs. 22 minutes) and a longer half-life (154 minutes vs. 121 minutes) compared to the medium disintegrating version. These data further demonstrate the ability of the NanoTab® to modulate PK based on excipient selection.

Alfentanil NanoTabs® resulted in a bioavailability of 94% compared to IV alfentanil and a coefficient of variation of 5% for the AUC, 7% for $C_{max}$ and 28% for $T_{max}$. The Therapeutic Time Ratio was calculated as 0.33, compared to 0.04 for the IV alfentanil arm of this study (calculated using a published IV elimination half-life of 104 min for alfentanil in dogs). Therefore, the alfentanil NanoTab® formulation (as described in Example 6) produces an 8-fold improved Therapeutic Time Ratio over the IV alfentanil arm. The high bioavailability of this formulation again supports the claim that minimal swallowing of drug occurs with use of the NanoTab®.

In Vitro NanoTab® Tests

Bioadhesion

The mucoadhesive strength is determined by attaching the tablets to the bottom of a hanging platform and determining the force required to detach the formulations from a porcine buccal mucosa substrate. The mucoadhesive testing system consisting of a precision load cell (GS-500 Tranducer techniques, Temecula, Calif.) and a hook attachment. The load cell generates analogue signals, which are converted into digital signals through a data acquisition system equipped with an A/D converter (Model 500 A, Keithley Metrabyte, Taunton, Mass.) and an IBM computer. Data were analyzed using EasyLx software (Keithley Metrabyte). A hanging platform comprised of a glass slide attached with plastic plunger (8 cm) on the top and a circular-steel projection (0.5 cm) with flat surface on the bottom is attached to the load cell. A flat-surfaced tablet die serves as a lower static-platform. The mucosa is mounted onto the lower platform using a screw-clamp. To determine the force of adhesion, the optimum level of that variable is kept constant in the subsequent evaluations. Between each measurement, the mucosal surface is rinsed with 4 mL of purified water. The excess water is wiped with a soft tissue paper and the mucosa is wetted with a known volume of phosphate buffer of pH 6.8. The hanging platform with the film is brought down and placed over the surface of mucosa with a known applied force for a required time. The detachment force is measured and converted to N/cm2. Studies are performed in triplicate at room temperature (23-25° C.). Adhesion and peak detachment force can be used to evaluate the bioadhesive strength of dosage forms comprising various formulations of the invention.

Drug Dissolution Kinetics

Drug dissolution kinetics is determined by a standard USP dissolution apparatus, such as Type I, II and/or Type IV, suitably modified for a given dosage form such as a dosage form containing a very small amount of active drug. Drug release from the dosage form can be monitored using one of the standard analytical methods, such as UV spectrophotometry, HPLC or LC/MS. The dissolution medium is defined as a physiological buffer such as phosphate, Tris or other at a pH range between 6.5-7.8. A dosage form of the invention may be manufactured to have a dissolution time from 30 seconds up to 1 minute, 2 minutes, 3 minutes, 4 minutes, 5 minutes, 10 minutes, 15 minutes, 30 minutes, 1 hour, 2 hours, 4 hours, 8 hours or longer.

Dosage Form Erosion Kinetics

Dosage form erosion can be monitored by observing the disappearance over time of the sublingual NanoTab® by visual examination. Complete dosage form erosion may be evident by visual examination in about 30 seconds up to 1 minute, 2 minutes, 3 minutes, 4 minutes, 5 minutes, 10 minutes, 15 minutes, 30 minutes, 1 hour, 2 hours, 4 hours or as long as 8 hours or longer, dependent upon the patient and circumstances of drug administration as well as the intrinsic tablet excipients. It will be understood that the composition of the oral transmucosal formulations of the present invention may be adjusted to provide for both a range of doses and a range of erosion times to fit particular clinical situations.

Pharmaceutically Active Ingredient(s)

The invention provides small volume dosage forms or NanoTabs® for oral transmucosal delivery of a formulation comprising any drug that can be delivered by the oral transmucosal route and in an amount that is appropriate to the small size of the NanoTab®. One example of use of the NanoTabs® of the invention is with application to pain-relief When the NanoTabs® of the invention are used for treatment of pain, they will comprise a drug such as an opioid or opioid agonist, for the treatment of acute or break-through pain. Opioids are powerful analgesics and are utilized to treat both acute and chronic pain of moderate to severe intensity throughout the world. However, they can also have severe respiratory depressive effects if not used appropriately and they also suffer from a high abuse potential. In 1998, a total of 36,848 opiate exposures (pure and mixed preparations) were reported to U.S. poison control centers, of which 1227 (3.3%) resulted in major toxicity and 161 (0.4%) resulted in death. The predominant cause of morbidity and mortality from pure opioid overdoses is via respiratory complications.

Opioids are still widely used for the treatment of pain, and are generally delivered intravenously, orally, epidurally, transdermally, rectally and intramuscularly. Morphine and its analogues are commonly delivered intravenously and are effective against severe, chronic and acute pain.

Opioids exert their actions via the mu opioid receptor, which is located on peripheral nerve terminals, both pre- and post-synaptically in the spinal cord, brainstem, mid-brain and cortical regions associated with sensory and pain processing. The active agent in such formulations may include sufentanil, or a sufentanil congener such as alfentanil, fentanyl, lofentanil, carfentanil, remifentanil, trefentanil, or mirfentanil. One preferred embodiment utilizes sufentanil as the active agent. Another preferred embodiment utilizes a sufentanil congener as the active agent. Yet another preferred embodiment utilizes a combination of sufentanil and at least one additional agent for treatment of analgesia as the active agent. The active agent may also include any opioid or opioid agonist such as morphine or a derivative thereof.

A dosage form of the invention may comprise at least 0.001% percent by weight of the pharmaceutically active ingredient. The pharmaceutically active drug is typically present in a therapeutically effective amount from about 0.25 µg to 99.9 mg, from about 1 µg to 50 mg or from about 1 µg to 10 mg.

Preferably, the dosage form comprises from about at least 0.005% to as much as 99.9% by weight, e.g., from about 0.25 µg to 99.9 mg, from about 1 µg to 50 mg or from about 1 µg to 10 mg of sufentanil; a sufentanil congener such as alfentanil, fentanyl, lofentanil, carfentanil, remifentanil, trefentanil, or mirfentanil.

In alternative embodiments, a formulation of the invention includes a combination of two or more opioid analogues, such as sufentanil plus an opioid such as sufentanil, alfentanil, fentanyl, lofentanil, carfentanil, remifentanil, trefentanil or mirfentanil. Various opioid drugs have different pharmacokinetic profiles and different interactions with mu opioid receptor splice variants and, therefore, may be used in combination to enhance the therapeutic effect.

In alternative embodiments, the drug dosage form of the invention may include at least one opioid drug and one or more other drugs wherein the other drug may be an opioid or non-opioid drug. The non-opioid drug may be added to increase analgesic efficacy or to help deter abuse or to avoid opioid-induced side effects.

In some embodiments, the oral dosage formulations of the invention include an opioid antagonist, such as naloxone. In such embodiments, naloxone is provided in an appropriate concentration to inhibit activity of the opioid component of the formulation were it to be injected.

The invention finds utility in the treatment of both opioid naïve patients and opioid tolerant patients.

The term "opioid naïve patient" is used herein with reference to a patient who has not received repeated administration of an opioid substance over a period of weeks to months.

The term "opioid tolerant patient" as used herein means a physiological state characterized by a decrease in the effects of an opioid substance (e.g., analgesia, nausea or sedation) with chronic administration. An opioid substance is a drug, hormone, or other chemical substance that has analgesic, sedative and/or narcotic effects similar to those containing opium or its derivatives. If analgesic tolerance develops, the dose of opioid substance is increased to result in the same level of analgesia. This tolerance may not extend to side effects and side effects may not be well tolerated as the dose is increased.

In certain embodiments, the dosage form of the invention may comprise at least 0.001% percent by weight of the active ingredient, e.g., sufentanil, alfentanil, fentanyl, lofentanil, carfentanil, remifentanil, trefentanil, mirfentanil. Preferably, the dosage form comprises from about at least 0.005% to as much as 99.9% by weight of sufentanil, alfentanil, fentanyl, lofentanil, carfentanil, remifentanil, trefentanil or mirfentanil. The percentage of active ingredient(s) will vary dependent upon the size of the dosage form and nature of the active ingredient(s), optimized to obtain maximal delivery via the oral mucosal route. In some aspects of the invention more than one active ingredient may be included in a single dosage form.

In various embodiments, the formulation of the present invention generally provides appropriate pain relief in all types of patients including children, adults of all ages who are opioid tolerant or naïve and non-human mammals. The invention finds utility in both the in-patient and out-patient setting.

The use of sufentanil clinically has predominantly been limited to IV administration in operating rooms or intensive care units. There have been a few studies on the use of liquid sufentanil preparations for low-dose intranasal administration (Helmers et al., 1989; Jackson K, et al., J Pain Symptom Management 2002: 23(6): 450-452) and case reports of sublingual delivery of a liquid sufentanil preparation (Gardner-Nix J., J Pain Symptom Management. 2001 August; 22(2): 627-30; Kunz K M, Theisen J A, Schroeder M E, Journal of Pain and Symptom Management, 8:189-190, 1993). In most of these studies, the smallest dosing of sufentanil in adults was 5 mcg in opioid naïve patients. Liquid administered to the oral or nasal mucosa suffers from lower bioavailability and possibly a shorter duration of action as demonstrated by our Animal Studies (sublingual liquid) as well as the literature (nasal liquid drops—Helmers et al., 1989). Gardner-Nix describes only analgesic data (not pharmacokinetic data) produced by liquid sublingual sufentanil and describes the analgesic onset of liquid sublingual sufentanil occurring within 6 minutes but the duration of pain relief lasted only approximately 30 minutes. Prior to this patent application, no pharmacokinetic data has been published on the use of sublingual sufentanil in any dosage form.

Opioids are known to produce physical dependence, possible addictive behaviors and tolerance with long-term use. Cells exposed to opioids can demonstrate mu opioid receptor internalization (rapid endocytosis). The in vitro mu-opioid receptor endocytosis of a series of clinically used opioids was evaluated alone and in combination with morphine in human embryonic kidney (HEK) 293 cells (Koch et al., Mol. Pharmacol. 67(1):12-4, 2005). The results indicated that the endocytotic potency of opioid drugs is negatively correlated with their ability to cause receptor desensitization and opioid tolerance in HEK 293 cells and that opioids with high endocytotic efficacies might cause reduced opioid tolerance. The results shown in Koch et al., 2005 indicate that sufentanil is an opioid with high endocytotic efficacy and is therefore less likely to cause opioid tolerance than related opioid analogues tested.

Sufentanil (N-[(4-(Methoxymethyl-1-(2-(2-thienyl)ethyl)-4-piperidinyl)]-N-phenylpropanamide), is used as a primary anesthetic, to produce balanced general anesthesia in cardiac surgery, for epidural administration during labor and delivery and has been administered experimentally in both intranasal and liquid oral formulations. A commercial form of sufentanil used for IV delivery is the SUFENTA FORTE® formulation. This liquid formulation contains 0.075 mg/ml sufentanil citrate (equivalent to 0.05 mg of sufentanil base) and 9.0 mg/ml sodium chloride in water. It has a plasma elimination half-life of 148 minutes, and 80% of the administered dose is excreted in 24 hours.

Fentanyl (N-(1-phenethyl-4-piperidyl)-N-phenyl-propanamide) was first synthesized in Belgium in the late 1950s, and has an analgesic potency of about 80 times that of morphine. Fentanyl and its congeners are mu opiate agonists that were originally developed as anesthesia agents, and are often administered intravenously due to rapid onset of analgesia. Following intravenous administration, the analgesic action of fentanyl is more prompt and less prolonged than that of morphine and meperidine. Following transbuccal administration by a lozenge (e.g., Actiq®), consumption of the lozenge is usually complete within 30 minutes, the bioavailability is 50%, although the $T_{max}$ of the 200 mcg Actiq dosage ranges from 20-120 minutes displaying the erratic GI uptake due to swallowing of 75% of the drug (Actiq® package insert).

More recent publications on the $T_{max}$ of Actiq indicate that these original times were skewed towards more rapid onset (Fentora package insert indicates a range of $T_{max}$ for Actiq extending to 240 minutes). Fentora has a slightly improved PK profile, with a 65% bioavailability, due to swallowing of 50% of the drug. Therefore, one major disadvantage of this treatment is that substantial amounts of lozenge-administered fentanyl are swallowed by the patient. Fentanyl and other opiate agonists, have the potential for deleterious side effects including respiratory depression, nausea, vomiting and constipation. Since fentanyl has a 30% bioavailability from the GI route, this swallowed drug can contribute to the $C_{max}$ plasma levels to a significant degree and results in the erratic $C_{max}$ and $T_{max}$ observed with these products.

Although sufentanil and fentanyl have many similarities as potent mu-opioid receptor agonists, they have been shown to differ in many key ways. Multiple studies have demonstrated sufentanil to be in the range of 7-24 times more potent than fentanyl (SUFENTA® package insert; Paix A, et al. Pain, 63:263-69, 1995; Reynolds L, et al., Pain, 110:182-188, 2004). Therefore, sufentanil may be administered using a smaller dosage form, avoiding the increased saliva response of a larger dosage form and thereby minimizing swallowing of the drug and the minimal and variable GI uptake, which is associated with a larger dosage form.

In addition, the lipid solubility (octanol-water partition coefficient) of sufentanil (1778:1) is greater than fentanyl (816:1). Sufentanil also displays increased protein binding (91-93%) compared with fentanyl (80-85%) (SUFENTA® and Actiq® package inserts, respectively). Sufentanil has a pKa of 8.01, whereas the pKa of fentanyl is 8.43 (Paradis et al., Therapeutic Drug Monitoring, 24:768-74, 2002). These differences can affect various pharmacokinetic parameters, for example, sufentanil has been shown to have a faster onset of action and faster recovery times than fentanyl (Sanford et al., Anesthesia and Analgesia, 65:259-66, 1986). This is advantageous for the treatment of acute pain when repeated dosing is available, such as in the present invention. Use of sufentanil can result in more rapid pain relief with the ability to titrate the effect and avoid overdosing.

Importantly, sufentanil has been shown to produce endocytosis of the mu-opioid receptor 80,000 times more potently than fentanyl (Koch et al., Molecular Pharmacology, 67:280-87, 2005). The result of this receptor internalization is that neurons continue to respond to sufentanil more robustly over time than with fentanyl, suggesting that clinically less tolerance would develop to sufentanil compared to fentanyl with repeated dosing.

Sufentanil has been used experimentally in adults in the form of an oral liquid (Gardner-Nix J., 2001; Kunz et al., 1993), and as nasal drops (Helmers et al., 1989), and nasal spray (Jackson et al., 2002), as described above. No pharmacokinetic data has been published on sublingual sufentanil in any dosage form.

Congeners of sufentanil and fentanyl find use in the compositions and methods of the invention, examples of which include remifentanil and alfentanil.

Remifentanil is a potent fentanyl congener that is metabolized much more rapidly than fentanyl or sufentanil, but may be suitable for treatment of acute pain when delivered via a sustained-release formulation. A NanoTab® of the invention typically comprises from about 0.25 mcg to 99.9 mg of remifentanil. The dose ranges for the remifentanil formulation may include 0.1 mcg/kg-50 mcg/kg over a time period of 20 minutes, for example, for both adult and pediatric patients.

These dosages may be repeated at appropriate time intervals, which may be shorter than the time intervals for fentanyl or sufentanil.

Alfentanil is also a potent fentanyl congener that is rapidly metabolized but may be suitable for use in a sustained-release formulation. A NanoTab® of the invention typically comprises from about 10 mcg to about 10 mg of alfentanil. Appropriate dosing of alfentanil may be in the range of 1 mcg/kg-2000 mcg/kg over 20 minutes, for example, for both adult and pediatric patients. These dosages may be repeated at appropriate time intervals, which may be shorter than the time intervals for fentanyl or sufentanil.

Patients suffering from chronic painful conditions can also have intermittent exacerbations of their pain, requiring acute use of fast-acting breakthrough opioids in addition to their use of slow-onset time-release opioids for their baseline chronic pain.

Breakthrough pain or procedural pain can be intense for short periods of time, as short as 1 or 2 minutes or as long as 30 minutes or more, therefore there would be a significant advantage in providing an opioid formulation that produced more rapid clinically effective plasma levels with a more consistent and predictable period of effect, but also had a limited half-life to avoid excessive opioid dosing for short duration pain events.

Opioids remain the most powerful from of analgesics, however, improved forms are needed that have minimal side effects, and can be provided in a manner in which patient use can be easily tracked by the physician.

Using current treatment methods, pain control is attempted using a number of interventions, which generally include: patient-controlled analgesia (PCA), continuous epidural infusion (CEI), other types of acute pain control, palliative care pain control, and home health patient pain control. These methods meet with varying degrees of success with respect to duration of control, ease of treatment and safety versus side effects.

The need for rapid treatment of acute pain occurs in many different clinical situations, including post-operative recuperation, rheumatoid arthritis, failed back, end-stage cancer, etc. Post-operatively, for example, patients suffer from severe pain for the first few days followed by days of mild to moderate levels of pain.

The most common analgesic used to treat moderate to severe post-operative pain is IV morphine. This is either delivered on an "as needed" basis by a nurse to the patient by an IV injection or commonly a morphine syringe is placed in a PCA pump and the patient self-administers the opioid by pressing a button which has a lock-out feature. Other opioids, such as hydromorphone and fentanyl may also be used in this manner.

Treatment of acute pain is also necessary for patients in an outpatient setting. For example, many patients suffer from chronic pain and require the use of opioids on a weekly or daily basis to treat their pain. While they may have a long-acting oral or transdermal opioid preparations to treat their chronic underlying pain levels, they often need short-acting potent opioids to treat their severe breakthrough pain levels.

Treatment of acute pain is also necessary "in the field" under highly sub-optimal conditions. Paramedics or military medics often are required to treat severe acute pain in unsterile situations, where needles used for IV or IM administration can result in unintended needle sticks, risk of infection, etc. Oral opioid tablets often take 60 minutes to provide relief which is too long for someone in severe pain.

In a number of clinical settings, there is clearly a need for a formulation that produces effective pain relief in a manner that is titratable, may be used safely and conveniently, and provides pain relief for severe breakthrough or intermittent pain over an appropriate period of time.

The drug delivery dosage forms or formulations of the invention contain from about 0.25 to about 200 mcg of sufentanil per dosage form for oral transmucosal delivery. In one exemplary embodiment of the invention, each dosage form contains from about 0.25 to about 200 mcg of sufentanil, alone or combination with one or more other therapeutic agents or drugs.

As will be understood by those of skill in the art, the dose will be on the low end of the range for children and the high end of the range for adults dependent upon body mass, in particular when administered long term to opioid-tolerant adults. Small-volume oral transmucosal drug delivery dosage forms of sufentanil have not been described.

Exemplary formulations of the invention for administration to children (pediatric patients) contain from about 0.25 to about 120 mcg of sufentanil per dosage form. For example, a formulation of the invention for administration to children may contain about 0.25, 0.5, 1, 2.5, 4, 5, 6, 8, 10, 15, 20, 40, 60 or 120 mcg of sufentanil for oral transmucosal delivery. It follows that for pediatric patients, an exemplary dose range is from at least about 0.02 mcg/kg to about 0.5 mcg/kg with a preferable range of from about 0.05 to about 0.3 mcg/kg.

Exemplary formulations of the invention for administration to adults contain from about 2.5 to about 200 mcg of sufentanil per dosage form. For example, a formulation of the invention for administration to adults may contain about 2.5, 3, 5, 7.5, 10, 15, 20, 40, 60, 80, 100, 120, 140, 180 or 200 mcg or more of sufentanil for oral transmucosal delivery.

In yet another example of the invention, each dosage form contains from about 2 to about 1500 mcg of fentanyl, alone or combination with one or more other therapeutic agents or drugs. As will be understood by those of skill in the art, the dose will be on the low end of the range for children and the high end of the range for adults dependent upon body mass, in particular when administered long term to opioid-tolerant adults.

Exemplary dosage forms of the invention for administration to children (pediatric patients) contain from about 2 to about 900 mcg of fentanyl per dosage form. For example, a dosage form of the invention for administration to children may contain about 2, 3.75, 7.5, 18.75, 30, 37.5, 45, 60, 75, 112.5, 150, 300, 450 or 900 mcg of fentanyl for oral transmucosal delivery.

Exemplary dosage forms of the invention for administration to adults contain from about 18.75 to about 1500 mcg of fentanyl per dosage form. For example, a dosage form of the invention for administration to adults may contain about 18.75, 22.5, 37.5, 56, 75, 112.5, 150, 300, 450, 600, 750, 900, 1050, 1350 or 1500 mcg or more of fentanyl for oral transmucosal delivery.

In one exemplary embodiment, a dosage form for use in the treatment of pain may comprise from about 0.25 to about 200 mcg of sufentanil, from about 0.5 to about 120 mcg of sufentanil, from about 2.5 to about 40 mcg of sufentanil, from about 2.5 to about 15.0 mcg of sufentanil, from about 2.0 to about 1500 mcg of fentanyl, from about 20 to about 1200 mcg of fentanyl, or from about 100 to about 900 mcg of fentanyl.

The dosage forms of the invention contain from about 10 to about 10000 mcg of alfentanil per dosage form for oral transmucosal delivery. As will be understood by those of skill in the art, the dose will be on the low end of the range for children and the high end of the range for adults dependent upon body mass, in particular when administered long term to opioid-tolerant adults.

Exemplary dosage forms of the invention for administration to children (pediatric patients) contain from about 10 to about 6300 mcg of alfentanil per dosage form. For example, a dosage form of the invention for administration to children may contain about 10, 25, 50, 130, 210, 280, 310, 420, 600, 780, 1050, 2100, 3000 or 6300 mcg of alfentanil for oral transmucosal delivery.

Exemplary dosage forms of the invention for administration to adults contain from about 70 to about 10000 mcg of alfentanil per dosage form. For example, a dosage form of the invention for administration to adults may contain about 70, 140, 160, 210, 280, 310, 420, 600, 780, 1050, 2100, 3000, 6300 or 10000 mcg or more of alfentanil for oral transmucosal delivery.

In a different exemplary embodiment, a dosage form for use in the treatment of pain may comprise from about 0.25 to about 200 mcg of sufentanil in combination with from about 2 to about 1500 mcg of fentanyl or from about 0.25 to about 200 mcg of sufentanil or from about 2 to about 1500 mcg of fentanyl in combination with one or more additional drugs.

Following delivery of a single dose of a sufentanil-, alfentanil-, or fentanyl-containing dosage form of the invention to a human subject, the plasma level of sufentanil, alfentanil or fentanyl may reach a maximum level between 0 and 60 minutes, between 5 and 50 minutes or between 10 and 40 minutes after administration.

Methods for Delivery of Oral Transmucosal Dosage Forms

A device for NanoTab® delivery can use a variety of mechanical or electromechanical methods to expel the NanoTab® into the oral or sublingual space. For example the NanoTab® can be forcibly expelled by means of a spring, compressed air, or other mechanism once activated.

Methods of Making Oral Transmucosal Dosage Forms

Methods of making a drug-containing dosage forms for oral transmucosal delivery, such as a NanoTab® is also provided by the invention. By way of example, the method includes the steps of weighing the drug and one or more of bioadhesions, binders, hydrogel forming excipients, bulking agents, lubricants or glidants and factors that affect dissolution time, possibly powder grinding, dry powder mixing and tableting via direct compression.

Alternatively, a wet granulation process may be used. Such a method (such as high shear granulation process) involves mixing the active ingredient and possibly some excipients in a mixer. The binder may be one of the excipients added in the dry mix state or dissolved in the fluid used for granulating. The granulating solution or suspension is added to the dry powders in the mixer and mixed until the desired characteristics are achieved. This usually produces a granule that will be of suitable characteristics for producing dosage forms with adequate hardness, dissolution, content uniformity, and other physical characteristics. After the wet granulation step, the product is most often dried and/or then milled after drying to get a major percentage of the product within a desired size range. Sometimes, the product is dried after being wet sized using a device such as an oscillating granulator, or a mill. The dry granulation may then processed to get an acceptable size range by first screening with a sieving device, and then milling the oversized particles. In some instances, an appropriate glidant is added to improve the flow properties of the granules; suitable glidants include silicas (such as SILOID and SILOX silicas—trademarks of Grace Davison Products, Aerosil—trademark of Degussa Pharma).

Additionally, the formulation may be manufactured by alternative granulation processes, all known to those skilled in the art, such as spray fluid bed granulation, extrusion and spheronization or fluid bed rotor granulation.

It will be understood that the formulation will be converted into a dosage form for delivery to a subject using procedures routinely employed by those of skill in the art. The process for preparation of the dosage form is optimized in order to achieve high dose content uniformity, which is particularly important for the potent compounds, which are generally present in mass ratios of 0.01-10% w/w.

Many methods of making dosage forms for use in the invention are known in the art and may be employed in practicing the present invention, such as direct compression, wet granulation, etc.

A NanoTab® dosage form of the invention may or may not have a coating on the external surface of the dosage form.

Utility of the Small-Volume Oral Transmucosal Dosage Forms of the Invention.

The dosage forms of the invention find utility in delivery of any drug that can be administered by the oral transmucosal route. The small volume of an oral transmucosal dosage form or NanoTab® of the invention is that it provides for high bioavailability, low variability in $T_{max}$, low variability in $C_{max}$ and low variability in AUC. The NanoTabs® of the invention also provide for controlled dissolution, solubility and stability, resulting in controlled release of the drug over time resulting in prolonged plasma levels within the therapeutic window.

In one exemplary embodiment described in detail herein, the dosage forms of the invention find utility in treating a subject suffering from pain that may be associated with any of a variety of identifiable or unidentifiable etiologies. In this embodiment, the dosage forms of the invention find utility in suppression or mitigation of pain. The term "treatment" or "management" of pain is used here to generally describe regression, suppression, or mitigation of pain so as to make the subject more comfortable, as determined for example by pain score.

The term "acute pain" is used herein with reference to pain that is typically present for less than one month, however, in some cases pain that is present for as long as three months may also be considered to be "acute".

The term "chronic pain" is used herein with reference to pain that is typically present for longer than one month.

The dosage forms of the invention find particular utility in the treatment of acute pain or other conditions "in the field", i.e., under highly sub-optimal conditions. Paramedics or military medics often are required to treat severe acute pain or other injuries or conditions in non-sterile situations, where needles used for IV or IM administration can result in unintended needle sticks, risk of infection, etc. Oral opioid tablets often take 60 minutes to provide relief which is too long for someone in severe pain. The dosage forms of the invention find utility in addressing this need.

The dosage forms of the invention find further utility in pediatric applications, since the comfortable and secure nature of the dosage form will allow small children to readily accept this mode of therapy and will reliably deliver drug transmucosally. Specific examples include, but are not limited to, treatment of pediatric acute pain when IV access is not available or inconvenient, treatment of pediatric asthma when the child is not able to use an inhaled route of administration effectively, treatment of nausea when a child can not or will not swallow a pill, pre-procedural sedation when a child is NPO (no oral intake allowed) or a more rapid onset is required.

The dosage forms of the invention find further utility in veterinary applications. Specific examples include, but are not limited to, any treatment of an acute condition for which IV administration is not readily available or inconvenient, such as pain relief, anxiety/stress relief, pre-procedural sedation, etc.

Oral transmucosal drug delivery is simple, non-invasive, and can be administered by the caregiver or the patient with minimal discomfort. Generally, oral transmucosal delivery of pharmaceuticals is achieved using solid dosage forms such as lozenges or tablets, however, liquids, sprays, gels, gums, powders, and films and the like may also be used.

For certain drugs, such as those with poor bioavailability via the GI tract, such as many lipophilic opioids, oral transmucosal delivery may provide a better delivery route than GI delivery. For drugs such as lipophilic opioids, oral transmucosal delivery has shorter onset time (i.e., the time from administration to therapeutic effect) than does oral GI delivery and provides significantly improved bioavailability.

The following examples are provided to illustrate the invention and are not intended to limit any aspect of the invention as set forth above or in the claims below.

EXAMPLES

In Vivo Pharmacokinetics

The dosage forms for the NanoTabs® described above can be tested for in vivo drug pharmacokinetics in both humans and a suitable animal model following sublingual administration. The following examples demonstrate the ability of the NanoTab® dosage forms to allow a consistent absorption profile of sufentanil citrate following sublingual administration in human volunteers and an awake, alert Beagle dog model.

Example 1

Sublingual Sufentanil NanoTabs® Administered Sublingually in Adult Human Volunteers

TABLE 1

Sufentanil NanoTab ® Formulations Used in the Human Clinical Study

| Ingredient | #46 2.5 ug Sufentanil Base | | | #47 5.0 ug Sufentanil Base | | | #48 10.0 ug Sufentanil Base | | |
|---|---|---|---|---|---|---|---|---|---|
| | Mass in Batch (g) | Mass in tablet, mg | % Mass in tablet, w/w | Mass in Batch (g) | Mass in tablet, mg | % Mass in tablet, w/w | Mass in Batch (g) | Mass in tablet, mg | % Mass in tablet, w/w |
| Sufentanil Citrate | 0.3750 | 0.00375 | 0.068 | 0.7500 | 0.0075 | 0.136 | 1.5000 | 0.0150 | 0.273 |
| Mannitol 200SD | 406.600 | 4.066 | 73.931 | 406.300 | 4.063 | 73.866 | 405.500 | 4.055 | 73.727 |
| Poloxamer (Lutrol F68) | 11 | 0.110 | 2.000 | 11 | 0.110 | 2.000 | 11 | 0.110 | 2.000 |
| Polyox WSR 303 | 16.5 | 0.165 | 3.000 | 16.5 | 0.165 | 3.000 | 16.5 | 0.165 | 3.000 |
| PEG-8000 | 82.5 | 0.825 | 15.001 | 82.5 | 0.825 | 14.999 | 82.5 | 0.825 | 15.000 |
| Stearic Acid | 27.5 | 0.275 | 5.000 | 27.5 | 0.275 | 5.000 | 27.5 | 0.275 | 5.000 |
| Mg Stearate | 5.5 | 0.055 | 1.000 | 5.5 | 0.055 | 1.000 | 5.5 | 0.055 | 1.000 |
| Total | 549.9750 | 5.49975 | 100 | 550.0500 | 5.5005 | 100 | 550.0000 | 5.5 | 100 |
| Calculated Strength (Sufentanil base) | | 0.002506159 | | | 0.005012 | | | 0.010025 | |

A human clinical study was performed using healthy volunteers. The study was performed with 12 subjects (6 men and 6 women) using Sufentanil NanoTabs® (formulations #46-#48 shown in Table 1) manufactured to have a volume of 5 µL, a mass of approximately 5.5 mg, and determined to have a uniform size for all dosage strengths with dimensions of approximately 3 mm in diameter and 0.8 mm in thickness. Sufentanil NanoTabs® contained either 2.5 µg, 5 µg or 10 µg of sufentanil base corresponding to 3.7 µg, 7.5 µg or 15 µg of sufentanil citrate, respectively. All excipients were inactive and have GRAS ("generally recognized as safe") status. The sufentanil NanoTabs® were tested for sublingual use. Study staff administered individual NanoTabs® to a subject by placing them directly at the base of the frenulum using blunt-tipped forceps.

NanoTab® Attributes

Bioadhesion

The bioadhesion was measured as described earlier on the sufentanil clinical trial formulation (#46-#48) without the sufentanil component. The bioadhesion force required for displacement of the NanoTab® was measured as 0.046±0.01 $N/cm^2$.

In Vitro Evaluation of Dissolution

Figure 1:
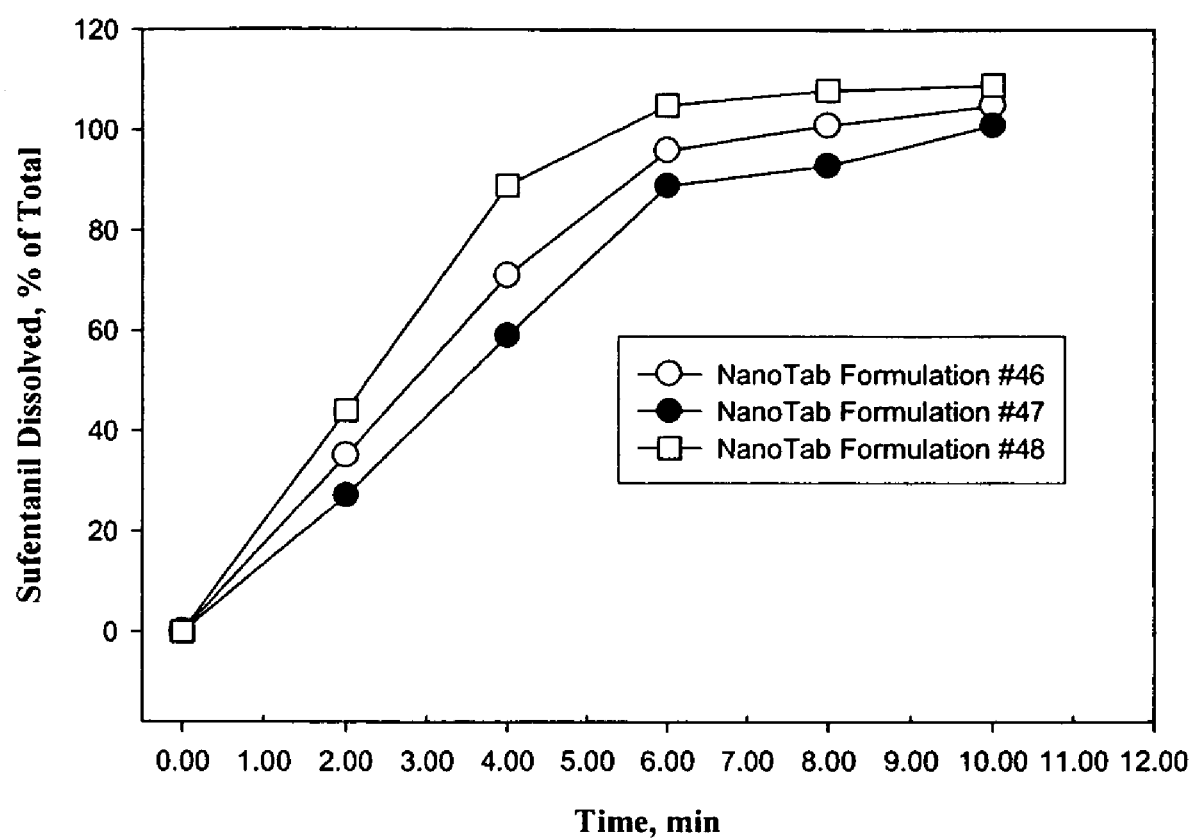
FIG. 1 is a graphic depiction of the in vitro dissolution kinetics of sufentanil NanoTab® formulations #46-#48 which were used in the human clinical study described in Example 1.

Sufentanil citrate dissolution from NanoTab® formulations #46, #47 and #48 was evaluated in a Type II in vitro dissolution system, as described earlier, and is show in FIG. 1 below.

For bioavailability calculations, intravenous sufentanil, 5 µg was diluted in 0.9% saline to a total volume of 20 mL, and was administered through an IV catheter as a continuous infusion over 10 minutes. Plasma samples were drawn from a different IV catheter at a remote location. This human trial was a cross-over design with wash-out periods between transitions from higher to lower doses. Subjects were blocked with the opioid antagonist naltrexone daily to avoid opioid-induced side-effects.

Day 0: IV sufentanil Infusion:
  Seventeen samples were collected:
−5.0 (before the start of infusion), 2.5, 5, 7.5, 10, 12.5, 15, 20, 30, 45, 60, 90, 120, 160, 320, 480 and 640 minutes
  Day 2: sublingual 2.5 µg sufentanil NanoTabs®;
  Seventeen samples:
−5.0 (before NanoTab® administration), 2.5, 5, 7.5, 10, 12.5, 15, 20, 30, 45, 60, 90, 120, 160, 320, 480 and 640 minutes
  Day 3: sublingual 5.0 µg sufentanil NanoTabs®;
  Seventeen samples:
−5.0 (before NanoTab® administration), 2.5, 5, 7.5, 10, 12.5, 15, 20, 30, 45, 60, 90, 120, 160, 320, 480 and 640 minutes
  Day 4: sublingual 10.0 µg sufentanil NanoTabs®;
  Seventeen samples:
−5.0 (before NanoTab® administration), 2.5, 5, 7.5, 10, 12.5, 15, 20, 30, 45, 60, 90, 120, 160, 320, 480 and 640 minutes
  Day 7: sublingual 5.0 µg sufentanil NanoTabs® repeated 4 times at 10 minute intervals;
  Twenty three samples:
−5.0 (before the first NanoTab® administration), 5, 7.5 minutes
10 (immediately prior to the second NanoTab® administration), 15, 17.5 minutes
20 (immediately prior to the third NanoTab® administration), 25, 27.5 minutes
30 (immediately prior to the fourth NanoTab® administration), 35, 40, 45, 50, 55, 60, 90, 120, 150, 190, 350, 510 and 670 minutes The total volume of blood required for pharmacokinetic sampling was approximately 455 mL.

Sufentanil concentrations in plasma samples were determined using a validated LC-MS/MS sufentanil human plasma assay. The assay demonstrated good inter-day precision and accuracy at the high, medium and low quality control sample concentrations.

Erosion Time

Figure 2:
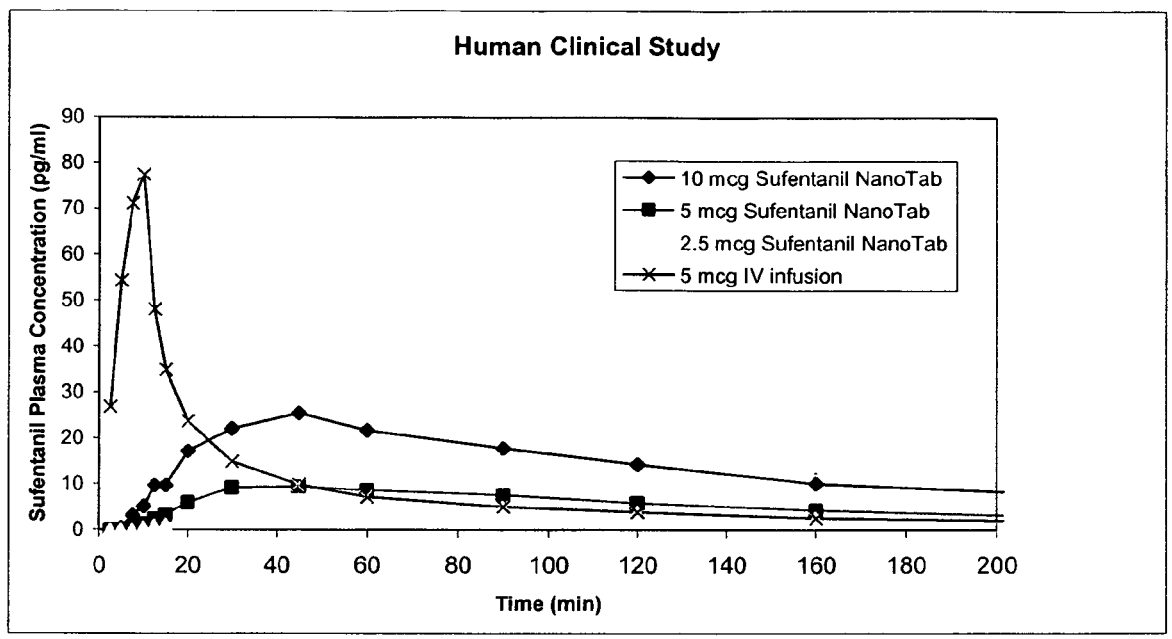
FIG. 2 is a graphic depiction of sufentanil plasma concentrations following intravenous dosing or sublingual single dose administration of three different strengths of sufentanil NanoTabs® in healthy human volunteers (n=12).

The NanoTabs® for this study eroded over a period of 10-30 minutes in all subjects. After placement of each sufentanil sublingual NanoTabs® in the sublingual cavity of the 12 healthy volunteers, a remarkably consistent pharmacokinetic profile was obtained for the three dosages (FIG. 2).

TABLE 2

PK Analyses of the IV (5 mcg) and Sublingual Sufentanil NanoTab ® Dosing Arms in the Human Clinical Study using Three Dosage Strengths (2.5 mcg = #46, 5 mcg = #47, 10 mcg = #48)

| Group | AUC (hr * ng/ml) (mean ± SD) | F (%) | Absorption Variability (% CV) | $C_{max}$ (ng/mL) | $T_{max}$ (hr) | Plasma Elimination Half-life (hr) | Therapeutic Time Ratio[1] |
|---|---|---|---|---|---|---|---|
| Intravenous Sufentanil | 0.0368 ± 0.0076 | — | 20.7 | 0.0813 ± 0.0281 | 0.16 ± 0.03 | 1.19 ± 0.18 | 0.067 |
| Sublingual Sufentanil NanoTab ® (Formulation #46) | 0.0178 ± 0.0044 | 97.8 | 24.7 | 0.0068 ± 0.0021 | 0.73 ± 0.13 | 1.65 ± 0.43 | 0.74 |
| Sublingual Sufentanil NanoTab ® (Formulation #47) | 0.0273 ± 0.0093 | 76.7 | 34.1 | 0.0109 ± 0.0035 | 0.77 ± 0.29 | 1.54 ± 0.57 | 0.75 |
| Sublingual Sufentanil NanoTab ® (Formulation #48) | 0.0705 ± 0.0194 | 98.2 | 27.5 | 0.0275 ± 0.0077 | 0.68 ± 0.22 | 1.71 ± 0.40 | 0.72 |

TABLE 2-continued

PK Analyses of the IV (5 mcg) and Sublingual Sufentanil NanoTab ® Dosing Arms in the
Human Clinical Study using Three Dosage Strengths (2.5 mcg = #46, 5 mcg = #47, 10 mcg = #48)

| Group | AUC (hr * ng/ml) (mean ± SD) | F (%) | Absorption Variability (% CV) | $C_{max}$ (ng/mL) | $T_{max}$ (hr) | Plasma Elimination Half-life (hr) | Therapeutic Time Ratio[1] |
|---|---|---|---|---|---|---|---|
| Repeat Dosing of #47 Sufentanil NanoTab ® every 10 min. × 4 | 0.1403 ± 0.0361 | 96.4 | 25.7 | 0.0464 ± 0.0124 | 1.04 ± 0.23 | 1.97 ± 0.30 | NA |

[1]Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from literature and is 148 min in humans for sufentanil.

Example 2

In Vivo Evaluation of Sublingual Sufentanil NanoTabs® in a Dog Model

The following Examples 2-5 are using the Beagle dog model and the formulations for the NanoTabs® all are using a NanoTab® with a total mass of 5.5 mg. The in vivo pharmacokinetics (PK) of sufentanil following sublingual administration of the 5 mcg NanoTabs® (formulation #44 for dogs, which is the same as the human formulation #47) described above were evaluated in a healthy Beagle dog model. Briefly, single 5 mcg NanoTabs® described above were administered sublingually in fully awake healthy dogs by direct placement in the sublingual cavity. A total of three dogs were evaluated. Following administration, the position of the NanoTab® in the sublingual cavity was observed visually at 5-15 minute intervals following administration. The sublingual sufentanil PK was compared with that of IV administered sufentanil at the same dose level.

Figure 3:
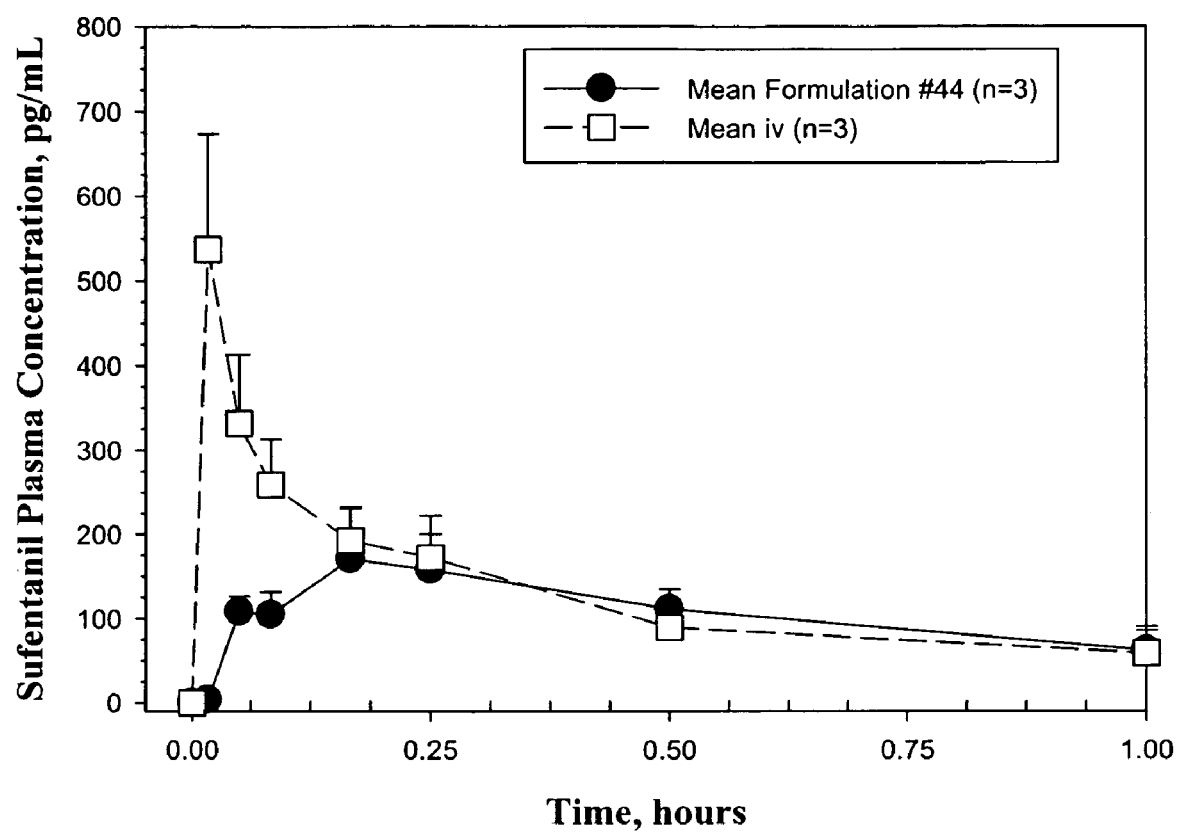
FIG. 3 is a graphic depiction of sufentanil plasma concentrations following sublingual administration of a sufentanil NanoTab® formulation #44 (equivalent to human #47 formulation; n=3) compared to intravenous sufentanil administration (n=3) in a healthy, conscious Beagle dog model. Error bars represents standard errors around the mean (SEM).

All dogs were catheterized via the cephalic vein for blood collections up to 2 hours post-dosing. Through the 2-hour post-dose blood collection, all dogs were fitted with an Elizabethan collar to prevent removal of the catheter. The catheter was removed following the 2-hour blood collection. The 4-, 8-, and 24-hour post-dose blood collection were collected from the cephalic or other suitable vein. Approximately 2 ml of blood were collected into pre-chilled tubes containing potassium EDTA at the following timepoints: prior to dosing and approximately 1, 3, 5, 10, 15, 30 min, 1, 2, 4, 8 and 24 hours post-dose. The samples were analyzed with the appropriately validated LC/MS/MS method for the determination of sufentanil citrate in dog plasma. The sufentanil plasma concentrations and the pharmacokinetic results are shown in FIG. 3 and Table 3.

TABLE 3

PK Analysis of Sufentanil Sublingual NanoTabs ® Compared to Intravenous Sufentanil in Beagle Dogs.

| Group | AUC (Mean ± SD) | F (%) | Absorption Variability (% CV) | $C_{max}$ (pg/mL) | $T_{max}$ (min) | Plasma Half-life (min) | Therapeutic Time Ratio[1] |
|---|---|---|---|---|---|---|---|
| Intravenous Sufentanil | 211.5 ± 48.2 | — | 22.8 | 536.7 ± 186.1 | 1.6 ± 0.6 | 10.3 ± 4.5 | 0.05 ± 0.02 |
| Sublingual Sufentanil NanoTab ® (Formulation #44) | 161.2 ± 23.1 | 74.8 ± 10.7 | 14.3 | 222.7 ± 25.9 | 11.7 ± 2.5 | 33.3 ± 5.8 | 0.28 ± 0.16 |

[1]Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from literature and is 139 min in beagle dogs for sufentanil.

Example 3

Exemplary Sufentanil Dosage Forms to Control Drug Release and In Vivo Pharmacokinetics For purposes of illustration, a longer duration NanoTab® dosage form (formulation #58) was prepared with sufentanil citrate in order to evaluate a slower rate of drug release and in vivo pharmacokinetics of a longer-acting dosage form. This slower disintegrating sufentanil NanoTab®, as described in Table 4 was prepared by direct compression and tested as described above. The range of erosion times in dogs was 35-120 minutes and the bioadhesion of the placebo formulation was measured as described above and determined to be $0.18 \pm 0.08$ N/cm$^2$.

Figure 4:
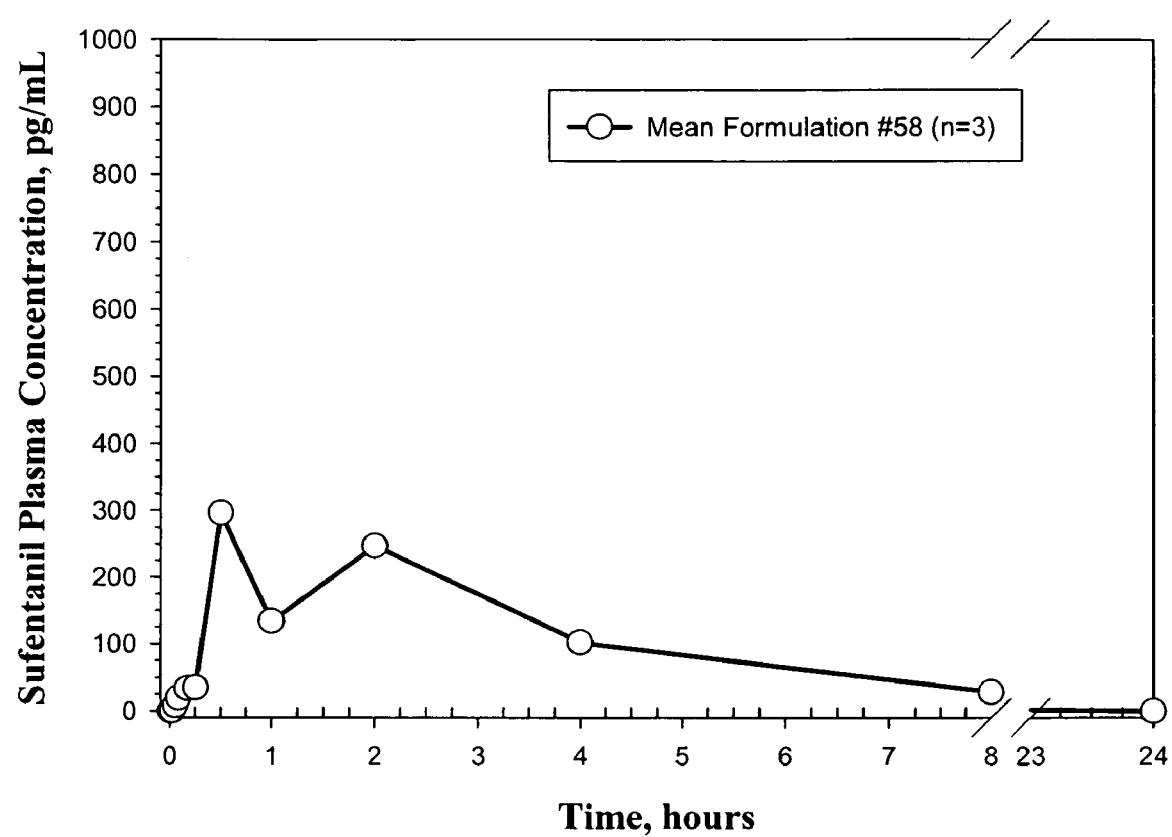
FIG. 4 is a graphic depiction of sufentanil plasma concentrations following sublingual administration of slowly disintegrating sufentanil NanoTab® formulation #58 (n=3) in a healthy, conscious Beagle dog model.

Sample analysis was performed using a validated LC/MS/MS method for analysis of sufentanil in dog plasma. Pharmacokinetic analysis was performed using a non-compartmental model of absorption. Sufentanil plasma concentrations are shown graphed in FIG. 4. The results of a limited PK analysis are shown in Table 5.

TABLE 4

Slow Disintegrating Sufentanil NanoTab ® Dosage Formulation.

| Composition | Formulation # 58 |
|---|---|
| Sufentanil citrate | 0.5456 |
| Mannitol | 40.3 |
| Carbopol 971 | 20.00 |
| PEG 8000 | 25.60 |
| HPMC | 10.00 |
| Polyox 303 | 2.60 |
| Mg Stearate | 1.00 |
| Total | 100.00 |

TABLE 5

PK Analyses for the Slow-Disintegrating Sublingual Sufentanil NanoTab ® in Beagle Dogs.

| Group | Plasma Half-life (min) | Therapeutic Time Ratio[1] |
|---|---|---|
| Sublingual NanoTab ® #58 | 205 ± 93.1 | 1.13 ± 0.69 |

[1] Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from the literature and is 139 min in beagle dogs for sufentanil.

Example 4

In Vivo Study of Sublingual Sufentanil Solution and Swallowing of Sufentanil NanoTabs® in a Dog Model

A. Evaluation of Bioavailability of Sufentanil Following Sublingual Administration of a Solution Dosage Form The bioavailability of sufentanil following sublingual administration from a solution as compared to that intravenously was evaluated in a healthy, conscious Beagle dog animal model, as indicated in Table 6. In both arms of the study the commercially available formulation of sufentanil citrate (Sufenta® 50 μg/mL) was used and was dosed at the same total dose of 5 μg of sufentanil base. Intravenous administrations (Group 1) were performed by single administration (n=3) of Sufenta® 50 μg/mL by bolus injection to the cephalic vein via a sterile needle and syringe of appropriate size. For the sublingual administrations (Group 2) the test article was prepared by appropriately diluting Sufenta® 50 μg/mL with 0.9% w/w to the same final dose of 5 μg of sufentanil base and was administered twice sublingually (n=6 total), with each dose separated by a minimum of a 2-day washout. Doses were slowly applied under the tongue, adjacent to the frenulum via a sterile syringe. Blood samples were collected from a jugular or other suitable vein prior to dosing and approximately 1, 3, 5, 10, 15, 30 min, 1, 2, 4, 8 and 24 hours post-dose. Approximately 2 mL of blood were collected per time-point into pre-chilled tubes containing $K_2$ EDTA. The samples were centrifuged at 3,000×g for approximately 10 minutes in a refrigerated centrifuge. Plasma was collected and frozen within 20 minutes of centrifugation at approximately −70° C. and was maintained at the same temperature until analysis. Sample analysis was performed using a validated LC/MS/MS method for analysis of sufentanil in dog plasma.

Figure 5:
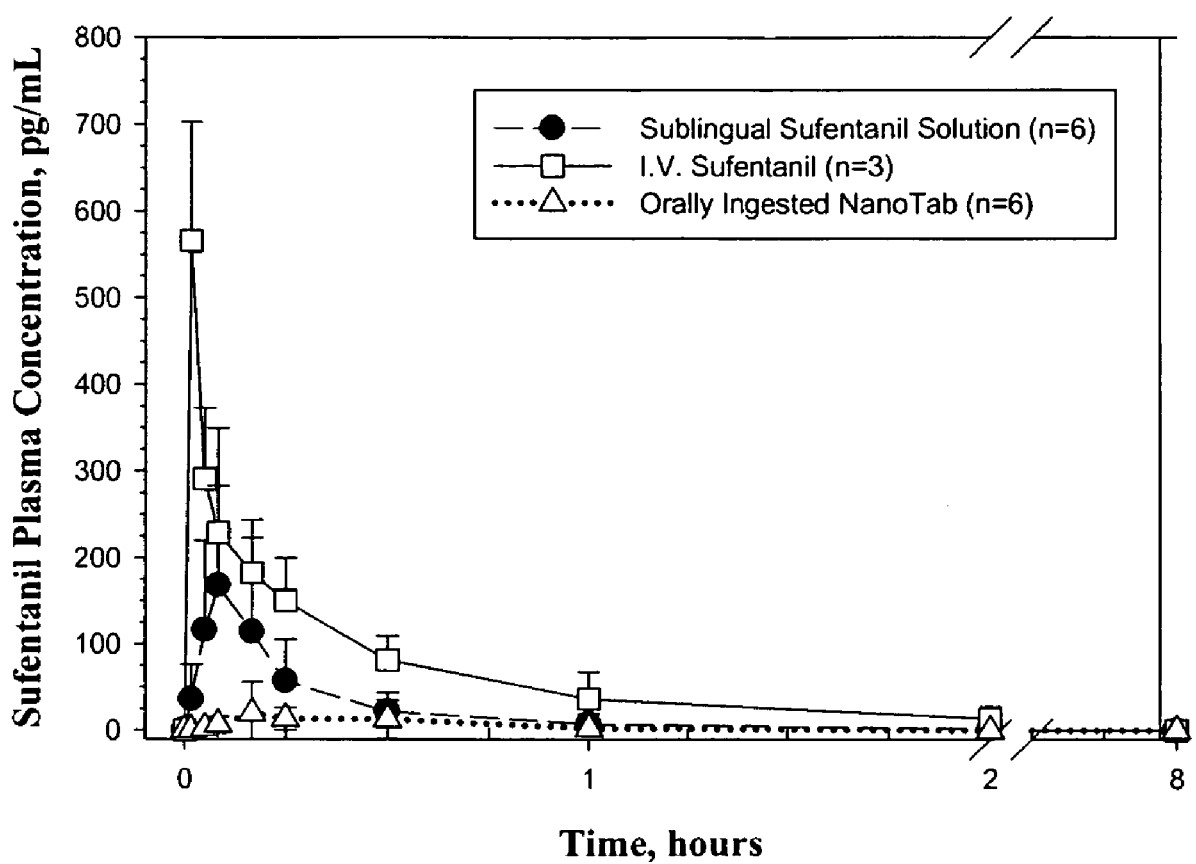
FIG. 5 is a graphic depiction of sufentanil plasma concentrations following sublingual administration of a sufentanil solution (n=6) or following oral ingestion of a sufentanil NanoTab® (n=6) compared to intravenous administration of sufentanil (n=3) in a healthy, conscious Beagle dog model. Error bars represents±standard error around the mean (SEM).

Pharmacokinetic analysis was performed using a non-compartmental model of absorption. The sufentanil plasma concentrations are graphed in FIG. 5. The results of the PK analysis are shown in Table 7.

B. Evaluation of Bioavailability of Sufentanil Following Oral Ingestion of a NanoTab®

The bioavailability of sufentanil following ingestion of a 5 mcg sufentanil NanoTab® (formulation #44, which is the same formulation as #47 used in the human study above) as compared to intravenous sufentanil administration was evaluated in a healthy, conscious Beagle dog animal model, as described in the previous example. A single 5 mcg NanoTab® was administered twice orally, with each dose separated by a minimum of a 2-day washout for a total of n=6 (Table 6). The NanoTabs® were placed manually as far back as possible in the throat and flushed with water to promote the swallow response in the animal. Pharmacokinetic analysis was performed using a non-compartmental model of absorption. The sufentanil plasma concentrations are shown graphed in FIG. 5. The results of the PK analysis are shown in Table 7.

TABLE 6

Organization of Test Groups

| Group | Treatment | Dose Level (μg)[a] | Route of Administration | Number of Animals[b] (Males) | Total Number of Animals, n |
|---|---|---|---|---|---|
| 1 | Sufentanil solution | 5.0 | IV | 3 | 3 |
| 2 | Sufentanil solution | 5.0 | Sublingual | 3[c] | 6 |
| 3 | Ingested Sufentanil NanoTab ® | 5.0 | Oral | 3[c] | 6 |

[a] = Expressed as a free base.
[b] = Same animals will be used for Groups 1 through 3 with a minimum 2-day washout period between dosing.
[c] = Group 2 & 3 animals were dosed twice with a minimum 2-day washout period for a total of n = 6
[d] = Normal (0.9% w/w) saline was used to dilute the test article (Sufenta ® 50 μg/mL) to the desired concentration.

TABLE 7

PK Analyses of Intravenously Administered Sufentanil Compared to a Sublingually Instilled Sufentanil Solution and an Ingested Sufentanil NanoTab ® in Beagle Dogs.

| Group | AUC (Mean ± SD) | F1 (%) | Absorption Variability (% CV) | $T_{max}$ (min) | $C_{max}$ (pg/mL) | Plasma Half-life (min) | Therapeutic Plateau Ratio[1] |
|---|---|---|---|---|---|---|---|
| Intravenous Sufentanil | 123.3 ± 49.3 | — | 21.8 | 1.0 ± 0.0 | 536.7 ± 186.1 | 2.8 ± 0.4 | 0.02 ± 0.0 |
| Sublingual Sufentanil solution | 58.3 ± 36.4 | 40.0 ± 32.7 | 81.8 | 4.3 ± 1.0 | 236.4 ± 170.0 | 8.3 ± 4.5 | 0.04 ± 0.02 |
| Ingested NanoTab ® | 15.9 ± 22.4 | 12.2 ± 15.3 | 134.2 | 14.6 ± 9.9 | 33.8 ± 33.2 | 22.5 ± 16.8 | 0.13 ± 0.09 |

[1]Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from the literature and is 139 min. in beagle dogs for sufentanil.

Example 5

In Vivo Evaluation of Sublingual Fentanyl NanoTabs® in a Dog Model

For purposes of demonstrating the superiority of the NanoTab® and its attributes over other commercial fentanyl oral transmucosal preparations, fentanyl NanoTab® dosage forms were prepared with fentanyl citrate in order to evaluate the rate of drug release and in vivo pharmacokinetics of various dosage forms. Both medium (formulation #60) and slow (formulation #62) disintegrating fentanyl NanoTabs®, as described in Table 8, were evaluated with both dosage forms prepared by direct compression. The erosion time in dogs of formulation #60 ranged from 5-20 minutes and the bioadhesion was measured at 0.056±0.01 N/cm² for the placebo formulation. The erosion time in dogs for formulation #62 ranged from 35-65 minutes and the bioadhesion for the placebo formulation was measured at 0.18±0.08 N/cm².

The commercially available formulation of fentanyl citrate (Sublimaze® 50 µg/mL) was used and was dosed IV at 70 µg of fentanyl base. Intravenous administrations were performed by single administration (n=3) of Sublimaze® 50 µg/mL by bolus injection to the cephalic vein via a sterile needle and syringe of appropriate size. For the sublingual administrations the NanoTabs® were administered sublingually (n=3 in each group) by placement under the tongue, adjacent to the frenulum via forceps. These parameters are shown in Table 9. The fentanyl plasma concentrations are graphed in FIG. 6. PK analysis was performed using a non-compartmental absorption model. The results of the PK analysis are shown in Table 10. Blood sampling and storage mirrored the conditions described earlier; sample analysis was performed using a validated LC/MS/MS method for analysis of fentanyl in dog plasma.

TABLE 8

Exemplary Fentanyl NanoTab ® Dosage Forms

| Composition | Formulation # 60 | Formulation # 62 |
|---|---|---|
| Fentanyl citrate | 2.00 | 2.00 |
| Mannitol | 55.00 | 38.80 |
| Carbopol 974 | 7.00 | 20.00 |
| PEG 8000 | 35.00 | 25.60 |
| HPMC | | 10.00 |
| Polyox 303 | | 2.60 |
| Mg Stearate | 1.00 | 1.00 |
| Total | 100.00 | 100.00 |

TABLE 9

Dosing Parameters for Fentanyl NanoTabs ® in Beagle Dogs

| Treatment | Dose Level (µg)[a] | Route of Administration | Dose Volume (mL) | Dose Concentration (µg/mL) | Number of Animals (Males) |
|---|---|---|---|---|---|
| Sublimaze ® | 70 | IV | 1.4 | 50[a] | 3 |
| Fentanyl NanoTab ® (#60) | 74.7 ± 3.8 | Sublingual (Medium-Disintegrating) | NA | NA | 2 |
| Fentanyl NanoTab ® (#62) | 69.3 ± 5.6 | Sublingual (Slow-Disintegrating) | NA | NA | 3 |

[a]Expressed as a free base.

TABLE 10

PK Analyses of Medium-Disintegrating (formulation #60) and Slow-Disintegrating (formulation #62) Fentanyl NanoTabs ® Compared to Intravenous Fentanyl Administration.

| Group | AUC (Mean ± SD) | F (%) | Absorption Variability (% CV) | $T_{max}$ (min) | $C_{max}$ (pg/mL) | Plasma Half-life (min) | Therapeutic Time Ratio[1] |
|---|---|---|---|---|---|---|---|
| Intravenous Fentanyl | 3155.8 ± 431.9 | — | 13.7 | 1.0 ± 0.0 | 7895.9 ± 6096 | 10.5 ± 9.6 | 0.04 ± 0.04 |

TABLE 10-continued

PK Analyses of Medium-Disintegrating (formulation #60) and Slow-Disintegrating (formulation #62) Fentanyl NanoTabs ® Compared to Intravenous Fentanyl Administration.

| Group | AUC (Mean ± SD) | F (%) | Absorption Variability (% CV) | $T_{max}$ (min) | $C_{max}$ (pg/mL) | Plasma Half-life (min) | Therapeutic Time Ratio[1] |
|---|---|---|---|---|---|---|---|
| Sublingual NanoTab ® #60 | 3213.6 ± 336.8 | 95.4 ± 10.0 | 10.5 | 22.5 ± 10.6 | 1188.2 ± 42.4 | 121.5 ± 19.1 | 0.46 ± 0.07 |
| Sublingual NanoTab ® #62 | 3092.6 ± 138.3 | 99.0 ± 4.4 | 4.5 | 50 ± 17.3 | 2226.9 ± 811.5 | 154.4 ± 52.6 | 0.46 ± 0.12 |

[1]Represents the relative time that the drug achieves therapeutic leves (above 50% of $C_{max}$) and it is calculated by the formula: TTR = (Time spent above 50% of $C_{max}$)/(IV Terminal elimination half-life). The denominator is obtained from the literature and is 244 min. in beagle dogs for fentanyl.

Example 6

In Vivo Evaluation of Sublingual Alfentanil HCl NanoTabs® in a Dog Model

For purposes of illustration of another drug use for the NanoTab®, an additional NanoTab® dosage form was prepared with alfentanil HCl in order to demonstrate the ability of the dosage forms described in this application to effectively improve the PK of alfentanil compared to that of the IV route of administration. The formulation composition, a medium disintegrating NanoTab®, is described in Table 11. The erosion time in dogs of formulation #63 was 20 minutes and the bioadhesion was measured at 0.056±0.01 N/cm² for the placebo formulation.

The dosing parameters for this study are shown in Table 12. The alfentanil plasma concentrations are graphed in FIG. 7. PK analysis was performed using a non-compartmental absorption model. The results of the PK analysis are shown in Table 13. Blood sampling and storage mirrored the conditions described earlier; sample analysis was performed using a validated LC/MS/MS method for analysis of alfentanil in dog plasma.

TABLE 11

Exemplary Alfentanil NanoTab ® Dosage Form

| Formulation #63 | % composition |
|---|---|
| Alfentanil HCl | 5.00 |
| Mannitol | 52.00 |
| Carbopol 974 | 7.00 |
| PEG 8000 | 35.00 |
| Mg Stearate | 1.00 |
| Total | 100.00 |

TABLE 12

Dosing Parameters for Administration of Sublingual Alfentanil NanoTabs ® and an Intravenous Alfentanil Solution in Beagle Dogs.

| Group | Treatment | Dose Level (μg)[a] | Route of Administration | Number of Animals (Males) |
|---|---|---|---|---|
| 1 | Alfentanil solution | 253 | IV | 3 |
| 2 | Alfentanil NanoTab ® | 239.0 ± 16.2 | Sublingual | 2 |

[a]= Expressed as a free base.
b = Same animals were used for Groups 1 and 2 with a minimum 2-day washout period between dosing.

TABLE 13

PK Analyses of Alfentanil Sublingual NanoTabs ® compared to Intravenous Alfentanil in Beagle Dogs.

| Group | AUC (Mean ± SD) | F (%) | Absorption Variability (% CV) | $T_{max}$ (min) | $C_{max}$ (ng/mL) | Plasma Half-life (min) | Therapeutic Time Ratio[1] |
|---|---|---|---|---|---|---|---|
| Intravenous Alfentanil | 15.3 ± 1.6 | — | 10.5 | 1 ± 0 | 139.1 ± 76.4 | 4.4 ± 2.4 | 0.04 ± 0.02 |
| Sublingual Alfentanil NanoTab ® | 14.4 ± 0.7 | 94.1 ± 4.6 | 4.9 | 15.0 ± 4.2 | 35.5 ± 2.6 | 40.8 ± 8.5 | 0.33 ± 0.07 |

[1]Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from literature and is 104 min. in beagle dogs.

What is claimed is:

1. A method of treating pain in a subject, comprising administering a small volume substantially homogeneous solid tablet by adhering said tablet to the oral mucosa of said subject, wherein: a) said tablet has a volume of from about 3 microliters (mcl) to about 15 mcl; b) said tablet comprises from about 2 to about 200 micrograms (mcg) of sufentanil and a bioadhesive material; c) said bioadhesive material provides for adherence of said tablet to the oral mucosa substantially throughout during the period of drug delivery; d) said tablet generates a minimal saliva response and minimal swallowing of drug; e) at least 50% of drug delivery occurs via the oral transmucosal route; and f) administration of said tablet to said subject results in a $T_{max}$ of from about 19.8 minutes to about 60 minutes.

2. The method according to claim 1, wherein said oral mucosal membrane is a sublingual membrane.

3. The method according to claim 1, wherein said oral mucosal membrane is a buccal membrane.

4. The method according to claim 1, wherein said tablet has a volume of less than 10 mcl.

5. The method according to claim 1, wherein said tablet comprises a dose of sufentanil selected from the group consisting of 5 mcg, 10 mcg, 15 mcg, 20 mcg, 40 mcg, 60 mcg, and 80 mcg, and 100 mcg.

6. The method according to claim 1, wherein oral transmucosal administration of said tablet to said subject results in a bioavailability of greater than 65%.

7. The method according to claim 1, wherein oral transmucosal administration of said tablet to said subject results in a bioavailability of greater than 75%.

8. The method according to claim 1, wherein oral transmucosal administration of said tablet to said subject results in a bioavailability of greater than 85%.

9. The method according to claim 1, wherein oral transmucosal administration of said drug tablet to said subject results in a $T_{max}$ with a coefficient of variation of less than 40%.

10. The method according to claim 1, wherein repeated oral transmucosal administration of said tablet to said subject, results in a $T_{max}$ that is shorter than the $T_{max}$ following a single oral transmucosal administration to said subject.

11. The method according to claim 1, wherein oral transmucosal administration of said tablet results in a therapeutic time ratio of from about 0.5 to about 2.0.

12. The method according to claim 1, wherein an amount of drug selected from the group consisting of at least 55%, at least 60%, at least 65%, at least 70%, at least 75%, at least 80%, at least 85%, at least 90%, at least 95%, at least 98% and at least 99% of the total amount of drug in said tablet is absorbed via the oral transmucosal route.

13. The method according to claim 12, wherein at least 60% of the total amount of drug in said tablet is absorbed via the oral transmucosal route.

14. The method according to claim 1, wherein said tablet is administered using a device.

15. The method according to claim 1, wherein said tablet is self-administered.

16. The method according to claim 14, wherein said tablet is administered using a single-does applicator.

17. The method of treating pain according to claim 1, wherein following said administering, pain relief is evident in said subject.

18. The method of claim 1, wherein said pain is acute pain, breakthrough pain or post-operative pain.

19. The method according to claim 18, wherein said pain is acute pain.

20. The method according to claim 19, wherein said subject is treated by a paramedic or military medic.

21. The method according to claim 19, wherein said subject is treated in the field.

22. The method according to claim 19, wherein said subject is treated under non-sterile conditions.

23. The method according to claim 5, wherein said tablet comprises 20 mcg of sufentanil.

24. The method according to claim 1, wherein said tablet comprises 30 mcg of sufentanil.

25. The method according to claim 1, wherein a single oral mucosal administration of said subject results in an average $T_{max}$ of 40.8±13.2 minutes.

26. The method of claim 1, wherein repeated administrations result in an area under the curve (AUC) with a coefficient of variation of less than 30%.

27. The method according to claim 1, wherein complete erosion of said tablet is evident by visual examination after a time selected from the group consisting of about 5 minutes, about 10 minutes and about 15 minutes following administration.

* * * * *